(12) United States Patent
Shoji

(10) Patent No.: US 10,017,734 B2
(45) Date of Patent: Jul. 10, 2018

(54) METHOD FOR PRODUCING DOPAMINERGIC NEURONS

(71) Applicant: TAKEDA PHARMACEUTICAL COMPANY LIMITED, Osaka-shi, Osaka (JP)

(72) Inventor: Masanobu Shoji, Fujisawa (JP)

(73) Assignee: TAKEDA PHARMACEUTICAL COMPANY LIMITED, Osaka-Shi, Osaka (JP)

( * ) Notice: Subject to any disclaimer, the term of this patent is extended or adjusted under 35 U.S.C. 154(b) by 0 days.

(21) Appl. No.: 14/910,018

(22) PCT Filed: Aug. 6, 2014

(86) PCT No.: PCT/JP2014/071352
§ 371 (c)(1),
(2) Date: Feb. 4, 2016

(87) PCT Pub. No.: WO2015/020234
PCT Pub. Date: Feb. 12, 2015

(65) Prior Publication Data
US 2016/0177260 A1  Jun. 23, 2016

(30) Foreign Application Priority Data
Aug. 6, 2013  (JP) .................. 2013-163062

(51) Int. Cl.
  *C12N 5/0793*  (2010.01)
  *A61K 35/30*  (2015.01)
(52) U.S. Cl.
  CPC ............ *C12N 5/0619* (2013.01); *A61K 35/30* (2013.01); *C12N 2500/38* (2013.01); *C12N 2501/01* (2013.01); *C12N 2501/16* (2013.01); *C12N 2501/727* (2013.01)
(58) Field of Classification Search
None
See application file for complete search history.

(56) References Cited

U.S. PATENT DOCUMENTS

2012/0094381 A1  4/2012  Chambers et al.
2015/0250825 A1  9/2015  Cooper et al.

FOREIGN PATENT DOCUMENTS

| WO | 2004081172 A2 | 9/2004 |
| WO | 2010108008 A2 | 9/2010 |
| WO | 2013067362 A1 | 5/2013 |
| WO | 2013187416 A1 | 12/2013 |
| WO | 2014124527 A1 | 8/2014 |

OTHER PUBLICATIONS

Extended European Search Report dated Nov. 18, 2016 corresponding to application No. 14834874.1-1402/3031908.
Fasano CA et al., "Efficient derivation of functional floor plate tissue from human embryonic stem cells." Cell Stem Cell. Apr. 2, 2010; 6(4):336-47.
Kriks S et al., "Floor Plate-derived Dopamine Neurons from hESCs Efficiently Engraft in Animal Models of PD." HHS Public Access Author Manuscript Jun. 22, 2012; 1-13.
Kirkeby A et al, "Generation of regionally specified neural progenitors and functional neurons from human embryonic stem cells under defined conditions." Cell Rep. Jun. 28, 2012; 1(6):703-14.
Xi J et al., "Specification of midbrain dopamine neurons from primate pluripotent stem cells." Stem Cells. Aug. 2012; 30(8):1655-63.
Denham M et al., "Glycogen synthase kinase 3β and activin/nodal inhibition in human embryonic stem cells induces a pre-neuroepithelial state that is required for specification to a floor plate cell lineage." Stem Cells. Nov. 2012; 30(11):2400-11.
Hwang DY et al., "Human ES and iPS cells as cell sources for the treatment of Parkinson's disease: current state and problems." J Cell Biochem. Feb. 1, 2010; 109(2):292-301.
Kriks S. et al., "Dopamine neurons derived from human ES cells efficiently engraft in animal models of Parkinson's disease." Nature. Nov. 6, 2011; 480(7378):547-51.
Jaeger I et al., "Temporally controlled modulation of FGF/ERK signaling directs midbrain dopaminergic neural orogenitor fate in mouse and human pluripotent stem cells." Development. Oct. 2011; 138(20):4363-74.
Kupershmidt L. et al., "The neuroprotective effect of Activin A and B: implication for neurodegenerative diseases." J Neurochem. Nov. 2007; 103(3):962-71.
Suzuki K et al., "Activin A induces neuronal differentiation and survival via ALK4 in a SMAD-independent manner in a subpopulation of human neuroblastomas." Biochem Biophys Res Commun. Apr. 9, 2010; 394(3):639-45.
Doi D. et al., "Isolation of human induced pluripotent stem cell-derived dopaminergic progenitors by cell sorting for successful transplantation." Stem Cell Reports. Mar. 6, 2014; 2(3):337-50.
Fedele S et al., "Long-Term Expansion of Dopaminergic Progenitors From Human Induced Pluripotent Stem Cells (IPSCS) and Differentiation Into Dopaminergic Neurons In-Vitro" The International Society for Stem Cell Research (ISSCR) 12th Annual Meeting, 2014, Poster Presentation II, Board No. T-2186 (https://ep70.eventpilotadmin.com/web/page.php?page=Search &project=ISSCR14#/web/page.php?page=Session &project=ISSCR14&id=P20756).
Brewer, "Serum-Free B27/Neurobasal Medium Supports Differentiated Growth of Neurons From the Striatum, Substantia Nigra, Septum, Cerebral Cortex, Cerebellum, and Dentate Gyrus", Journal Of Neuroscience Research, vol. 42, pp. 674-683, 1995.

(Continued)

*Primary Examiner* — James D Schultz
(74) *Attorney, Agent, or Firm* — Nath, Goldberg & Meyer; Joshua B. Goldberg; Scott H. Blackman

(57) ABSTRACT

The present invention provides a method of more efficiently producing a high-quality dopaminergic neuron from neural progenitor cells, specifically, a production method of a dopaminergic neuron including a step of culturing neural progenitor cells in a medium containing (i) a cAMP analog and (ii) a MEK inhibitor. Moreover, the present invention also provides a medicament containing a dopaminergic neuron obtained by the method, and a reagent and a kit to be used for the method.

10 Claims, 10 Drawing Sheets
(7 of 10 Drawing Sheet(s) Filed in Color)

(56) References Cited

OTHER PUBLICATIONS

Ying, et al., "Defined Conditions for Neural Commitment and Differentiation", Methods in Enzymology, vol. 365, 2003.
Shi, et al., "Directed differentiation of human pluripotent stem cells to cerebral cortex neurons and neural networks", Nature Protocols, vol. 7, No. 10, pp. 1836-1846, 2012.
Maroof, et al., "Directed Differentiation and Functional Maturation of Cortical Interneurons from Human Embryonic Stem Cells", Cell Stem Cell, vol. 12, pp. 559-572, May 2013.
ThermoFisher Scientific, PSC Dopaminergic Neuron Differentiation Kit, User Guide, Catalog No. A3147701, A3165801, A3147401, Revision 1. 0.
ICell DopaNeurons User's Guide, Cellular Dynamics International, Document ID: X1003.
BrainPhys Neuronal Medium, Stemcell Technologies, https://www.stemcell.com/brainphys-neuronal-medium.html.
Gemini Bio-Products, Gem21 NeuroPlex Serum-Free Supplement, Product Usage, Catalog #: 400-160.
Kriks, et al., "Floor plate-derived dopamine neurons from hESCs efficiently engraft in animal models of PD", Nature, vol. 480, No. 7378, pp. 547-551, 2012.

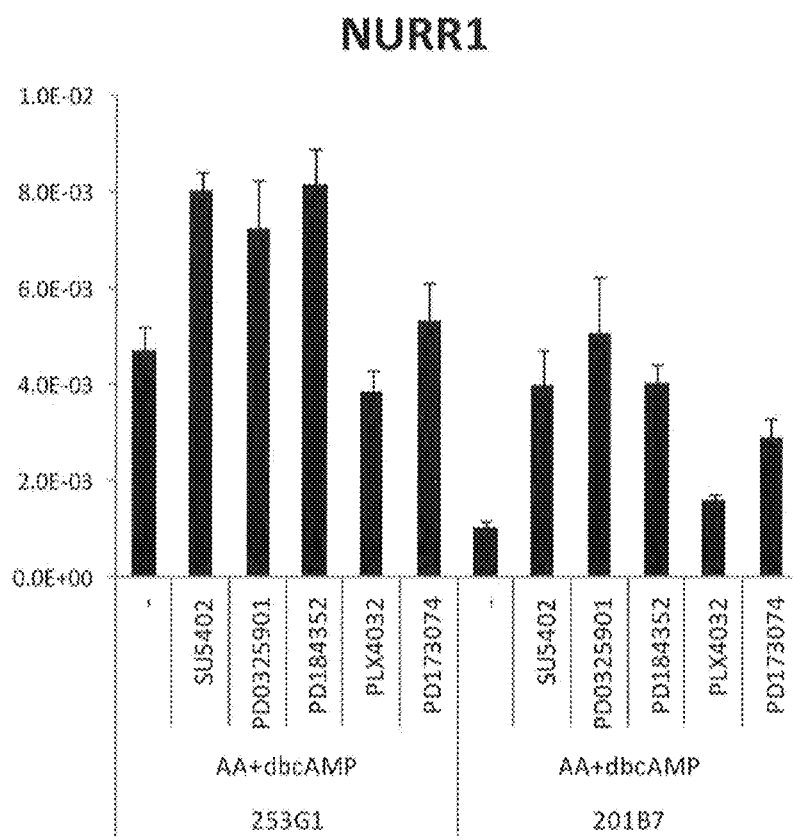

METHOD FOR PRODUCING DOPAMINERGIC NEURONS

This is a National Phase Application filed under 35 U.S.C. 371 as a national stage of PCT/JP2014/071352, filed Aug. 6, 2014, and claiming the benefit from Japanese Application No. 163062/2013, filed Aug. 6, 2013, the content of which is hereby incorporated by reference in its entirety.

The file of this patent contains at least one drawing executed in color. Copies of this patent with color drawing(s) will be provided by the Patent and Trademark Office upon request and payment of the necessary fee.

TECHNICAL FIELD

The present invention relates to a production method of a dopaminergic neuron. Moreover, the present invention also provides a medicament containing a dopaminergic neuron obtained by the method, and reagent and kit to be used for the method.

BACKGROUND OF THE INVENTION

Dopamine (3,4-dihydroxyphenylethylamine) is a biological molecule having a variety of actions, and mainly functions as a neurotransmitter in the central nervous system. In the body, dopamine is intracellularly biosynthesized by the action of two enzymes of tyrosine hydroxylase and DOPA decarboxylase with amino acid tyrosine as the origin.

Dopaminergic neuron is a neuron that synthesizes and releases dopamine as a neurotransmitter. In the brain, it is mainly present in the midbrain, and partly in the hypothalamus. Dopaminergic neuron present in the midbrain plays an important role in motility and emotional control. When midbrain dopaminergic neuron is degenerated or drops out, for example, severe neurodegenerative diseases such as Parkinson's disease and the like can be induced. One of the therapeutic approaches most expected to treat such neurodegenerative disease is a cell transplantation therapy including transplantation of a dopaminergic neuron to the target.

As a method for obtaining a dopaminergic neuron, a method including differentiating stem cells such as embryonic stem cell (sometimes to be referred to as ES cell in the present specification), induced pluripotent stem cell (sometimes to be referred to as iPS cell in the present specification) and the like into neuroectoderm, and further inducing differentiation into dopaminergic neuron is known at present.

Recently, it has been reported that a midbrain dopaminergic neuron is produced from floor plate cells. In addition, there have successively been reported a method including differentiating stem cells into floor plate cells by using two kinds of SMAD (Small Mothers Against Decapentaplegic) signaling inhibitors to obtain a midbrain dopaminergic neuron (patent document 1, non-patent document 1), a method for inducing a midbrain dopaminergic neuron by inducting floor plate cells from human stem cells and culturing the floor plate cells together with a neurotrophic factor (patent document 2, non-patent documents 2-4), and a method for efficiently inducing floor plate cells by reacting human ES cells with a GSK3 beta inhibitor and an activin/Nodal inhibitor (non-patent document 5).

However, the production efficiency of the dopaminergic neurons obtained by these methods remains low, and also, the cells are functionally insufficient since they cannot reproduce, in vitro, the responsiveness to oxidative stress and drug stimulation, and the like. Therefore, the development of a method for efficiently obtaining a high-quality dopaminergic neuron is still desired.

DOCUMENT LIST

Patent Documents

[patent document 1] US-B-2012/0094381
[patent document 2] WO 2013/067362

Non-Patent Documents

[non-patent document 1] Fasano et al., Cell Stem Cell 6 (2010) 336-347
[non-patent document 2] Kriks et al., Nature 480 (2011) 547-553
[non-patent document 3] Kirkeby et al., Cell Reports 1 (2012) 703-714
[non-patent document 4] Xi et al., Stem Cells 30 (2012) 1655-1663
[non-patent document 5] Denham et al., Stem Cells 30 (2012) 2400-2411

SUMMARY OF THE INVENTION

Problems to be Solved by the Invention

An object of the present invention is to provide a method for more efficiently producing a high-quality dopaminergic neuron. The present invention further aims to provide a medicament containing a dopaminergic neuron obtained by the method, as well as a reagent and a kit to be used for the method.

Means of Solving the Problems

In view of the above-mentioned problems, the present inventors have conducted intensive studies and found that a dopaminergic neuron can be produced at a high density and with good reproducibility by culturing neural progenitor cells in a medium containing (i) a cAMP analogue and (ii) a MEK inhibitor. Furthermore, they have confirmed that the obtained dopaminergic neuron is a high-quality dopaminergic neuron having the same phenotypic characteristics and functions as those of a dopaminergic neuron in vivo and the like, which resulted in the completion of the present invention.

Accordingly, the present invention provides the following.

[1] A production method of a dopaminergic neuron(s), comprising subjecting floor plate cells to the following step (1):
(1) a step of culturing in a medium containing (i) a cAMP analogue and (ii) a MEK inhibitor;
[2] The production method according to the above-mentioned [1], wherein the medium is a medium further containing ascorbic acid or a salt thereof;
[3] The production method according to [2], wherein the medium is a medium further containing an activator of activin receptor-like kinase-4,7;
[4] The production method according to [1], wherein the cAMP analogue is dibutyryl-cAMP;
[5] The production method according to [1], wherein the MEK inhibitor is
(i) N-((2R)-2,3-dihydroxypropoxyl-3,4-difluoro-2-[(2-fluoro-4-iodo-phenyl)amino]benzamide (PD0325901), (ii)  2-(2-chloro-4-iodophenylamino)-N-cyclopropylmethoxy-3,4-difluorobenzamide (PD184352), or
(iii) 2-[(1,2-dihydro-2-oxo-3H-indol-3-ylidene)methyl]-4-methyl-1H-pyrrole-3-propanoic acid (SU5402);

[6] The production method according to [3], wherein the activator of activin receptor-like kinase-4,7 is activin;

[7] The production method according to [3], wherein the cAMP analogue is dibutyryl-cAMP, the MEK inhibitor is
(i) N-[(2R)-2,3-dihydroxypropoxy]-3,4-difluoro-2-[(2-fluoro-4-iodo-phenyeamino]benzamide (PD0325901),
(ii) 2-(2-chloro-4-iodophenylamino)-N-cyclopropylmethoxy-3,4-difluorobenzamide (PD184352), or
(iii) 2-[(1,2-dihydro-2-oxo-3H-indol-3-ylidene)methyl]-4-methyl-1H-pyrrole-3-propanoic acid (SU5402), and
the activator of activin receptor-like kinase-4,7 is activin;

[8] A medicament comprising a dopaminergic neuron(s) obtained by the production method according to [1];

[9] A reagent for producing a dopaminergic neuron(s) from floor plate cells, comprising (i) a cAMP analogue and (ii) a MEK inhibitor;

[10] A kit for producing a dopaminergic neuron(s) from floor plate cells, comprising (i) a cAMP analogue and (ii) a MEK inhibitor;

[11] use of (i) a cAMP analogue and (ii) a MEK inhibitor for producing a dopaminergic neuron(s) from floor plate cells.

Effect of the Invention

According to the present invention, a high-quality dopaminergic neuron can be produced more efficiently from neural progenitor cells. The dopaminergic neuron produced by the present invention has phenotypic characteristics and functions similar to those of dopaminergic neurons in vivo, since it shows responsiveness to oxidative stress and drug stimulation that has not been observed in dopaminergic neurons produced by conventional methods, and the like. Therefore, the dopaminergic neuron produced by the present invention can achieve a high engrafted rate and is extremely useful for a cell transplantation therapy for treating a disease caused by decreased production (release) of dopamine, for example, neurodegenerative diseases such as Parkinson's disease and the like, as well as can be used for various applications such as screening for a compound useful for the prophylaxis and/or treatment of said diseases, toxicity evaluation of compounds, verification of drug discovery targets, analysis of disease mechanism and the like.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 8 shows the results of expression variation of NURR1, which were obtained by inducing differentiation of floor plate cells, culturing the cells by adding various MEK inhibitors (including FGFR inhibitors) in addition to ascorbic acid (AA) and dibutyryl-cAMP(dbcAMP) from 13 days after the induction, and examining the expression variation by quantitative RT-PCR on day 45. As the cell lines, 253G1 strain and 201B7 strain were used. The value of the Y axis shows the copy number of each gene normalized with the copy number of GAPDH, and the error bar shows standard deviation.

FIG. 9 shows a schematic drawing of a method of inducing differentiation from human iPS cell into floor plate cells and dopaminergic neuron.

DETAILED DESCRIPTION OF THE INVENTION

Figure 1:
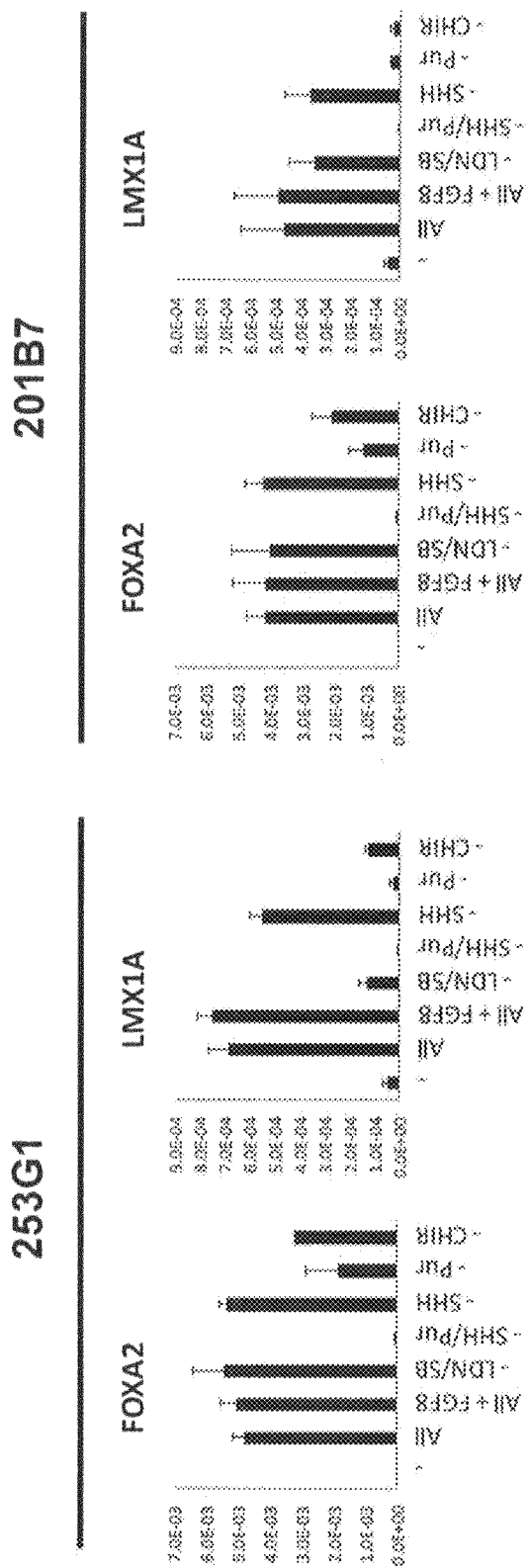
FIG. 1 shows the results of expression variation of a floor plate cell marker, which were obtained by inducing differentiation of floor plate cells by using Neuro/B27 added with various combinations of differentiation inducing factors and examining the expression variation by quantitative RT-PCR on day 13 of culture. [−] shows no addition of each differentiation inducing factor, [All] shows conditions using all 5 kinds of LDN193189 (LDN), SB431542 (SB), Sonic Hedgehog (SHH), purmorphamine (Pur) and CHIR99021 (CHIR). [−factor name] shows conditions without each factor. As the cell lines, 253G1 strain and 201B7 strain were used. The value of the Y axis shows the copy number of each gene normalized with the copy number of GAPDH, and the error bar shows standard deviation.

The present invention is explained below. The terms used in the present specification have the same meanings as those generally used in the pertinent field, unless particularly indicated.

In the present specification, the "dopaminergic neuron" means a neuron having an ability to produce dopamine (3,4-dihydroxyphenylethylamine) Dopaminergic neuron does not need to produce dopamine all the time, but only needs to have dopamine production capability. The amount of dopamine to be produced is not particularly limited.

Of the dopaminergic neurons in vivo, particularly dopaminergic neuron present in the midbrain such as substantia nigra pars compacta, ventral tegmentum and the like can be characterized by the expression of a particular cell marker in vitro, such as tyrosine hydroxylase(TH), FOXA2 (forkhead box A2), NURR1 (Nuclear Receptor-related 1) gene/protein and the like. In addition, the above-mentioned dopaminergic neuron present in the midbrain can also be characterized by the expression of a particular cell marker in vitro, such as TH, FOXA2, LMX1A (LIM homeobox transcription factor 1 alpha), NURR1 gene/protein and the like.

The "dopaminergic neuron" obtained by subjecting floor plate cells to the production method of the present invention is a dopaminergic neuron present in the midbrain (i.e., midbrain dopaminergic neuron).

In the present specification, the "neural progenitor cell" refers to a cell capable of producing a dopaminergic neuron after differentiation, which is specifically, for example, floor plate cells, a neuroectoderm cell characterized by an expression marker, such as intermediate filament protein Nestin and the like, and the like, most preferably a floor plate cell.

In the present specification, the "floor plate cell" means a morphologically specialized organizer cell located from the spinal cord to the diencephalon, in the ventral midline of the neural tube. Of the floor plate cells, particularly one located in the ventral midbrain can be characterized in vitro by the expression of a particular cell marker such as FOXA2, LMX1A gene/protein and the like.

In the present specification, the "stem cell" refers to a cell that can be cultured in vitro and can be differentiated into cells of plural lineages constituting the body. It specifically includes ES cell, pluripotent stem cell derived from fetal primordial germ cell (EG cell: Proc Natl Acad Sci USA. 1998, 95: 13726-31), pluripotent stem cell derived from testis (GS cell: Nature. 2008, 456: 344-9), induced pluripotent stem cell derived from somatic cell (induced pluripotent stem cells; iPS cell), and human pluripotent somatic stem cell (neural stem cell), preferably iPS cell and ES cell, more preferably iPS cell.

As the ES cell, an ES cell derived from any warm-blooded animal, preferably mammal can be used. Examples of the mammal include mouse, rat, guinea pig, hamster, rabbit, cat, dog, sheep, swine, bovine, horse, goat, monkey, and human. Preferable examples of the ES cell include ES cells derived from human.

Specific examples of the ES cell include an ES cell of a mammal and the like, which has been established by culturing an early embryo prior to implantation, an ES cell established by culturing an early embryo prepared by nucleus transplantation of the nucleus of a somatic cell, and an ES cell obtained by alteration of a gene on the chromosomes of these ES cells by a genetic engineering method.

Each ES cell can be prepared according to a method generally performed in the pertinent field, or a known document.

Mouse ES cell was established in 1981 by Evans et al (1981, Nature 292: 154-6) and Martin G R. et al. (1981, Proc Natl Acad Sci 78: 7634-8) and can be purchased from, for example, Sumitomo Dainippon Pharma Co., Ltd. (Osaka, Japan) and the like.

Human ES cell was established in 1998 by Thomson et al (Science, 1998, 282: 1145-7), and is available from WiCell Research Institute (website:http://www.wicell.org/, Madison, Wis., USA), US National Institute of Health, Kyoto University and the like and can be purchased from, for example, Cellartis (website:http://www.cellartis.com/, Sweden) and the like.

As an iPS cell, an iPS cell derived from any warm-blooded animal, preferably mammal, can be used. Examples of the mammal include mouse, rat, guinea pig, hamster, rabbit, cat, dog, sheep, swine, bovine, horse, goat, monkey, and human. Preferable examples of the iPS cell include an iPS cell derived from human.

Specific examples of the iPS cell include a cell that acquired multipotency as in ES cell, which can be obtained by introducing plural genes into a somatic cell such as skin cell and the like. For example, an iPS cell obtained by introducing Oct3/4 gene, Klf4 gene, c-Myc gene and Sox2 gene, and an iPS cell obtained by introducing Oct3/4 gene, Klf4 gene and Sox2 gene (Nat Biotechnol 2008; 26: 101-106). Other than these, a method of further decreasing transgene (Nature. 2008 Jul. 31; 454 (7204): 646-50), a method utilizing a low-molecular-weight compound (Cell Stem Cell. 2009 Jan. 9; 4(1): 16-9, Cell Stem Cell. 2009 Nov. 6; 5(5): 491-503), a method utilizing a transcription factor protein instead of gene (Cell Stem Cell. 2009 May 8; 4(5): 381-4) and the like.

The produced iPS cell can be used for the present invention irrespective of the production method thereof.

Examples of the human iPS cell line include, specifically, 253G1 strain (iPS cell line prepared by expressing OCT4/SOX2/KLF4 in skin fibroblast of 36-year-old female), 201B7 strain (iPS cell line prepared by expressing OCT4/SOX2/KLF4/c-MYC in skin fibroblast of 36-year-old female), 1503-iPS (297A1) (iPS cell line prepared by expressing OCT4/SOX2/KLF4/c-MYC in skin fibroblast of 73-year-old female), 1392-iPS (297F1) (iPS cell line prepared by expressing OCT4/SOX2/KLF4/c-MYC in skin fibroblast of 56-year-old male), NHDF-iPS (297 L1) (iPS cell line prepared by expressing OCT4/SOX2/KLF4/c-MYC in skin fibroblast of newborn boy) and the like.

1. Production Method of Dopaminergic Neuron

The present invention provides a production method of a dopaminergic neuron, comprising subjecting floor plate cells to the following step (1):
(1) a step of culturing in a medium containing (i) a cAMP (cyclic adenosine monophosphate) analogue and (ii) a MEK inhibitor (hereinafter sometimes to be referred to as the production method of the present invention).

A method of obtaining a neural progenitor cell to be used in the production method of the present invention is not particularly limited, and the cell can be directly recovered from the target animal embryo. To obtain a large amount of neural progenitor cell, it is preferably produced from a stem cell as a starting material.

A method of obtaining a neural progenitor cell from a stem cell is not particularly limited, and a method known per se such as a method including culturing pluripotent stem cell in the presence of a low molecular BMP inhibitor, a differentiation induction method by coculture with stromal cell (SDIA method) and the like can be utilized.

While the neural progenitor cell to be used in the production method of the present invention may be any as long as a dopaminergic neuron can be produced after differentiation, a floor plate cell is most preferably used as a starting cell. Therefore, in the following, a method of differentiating a stem cell into a floor plate cell is specifically described.

1-1. Method of Differentiating Stem Cell into Floor Plate Cell

This differentiation method includes a step of culturing stem cell in a medium containing a floor plate cell differentiation inducing factor.

In the present differentiation method (differentiation induction method), the stem cell is generally cultured on a culture vessel. Examples of the culture vessel to be used here include flask, tissue culture flask, dish, petridish, tissue culture dish, multidish, microplate, microwell plate, multiplate, multiwell plate, chamber slide, petri dish, tube, tray, culture bag, and roller bottle. Preferred are dish, petridish, tissue culture dish, multidish, microplate, microwell plate, multiplate, multiwell plate and the like. The culture vessel is preferably applied with a coating suitable for maintenance and culture of stem cells. Specifically, a culture vessel coated with a feeder cell or an extracellular substrate component is preferably used. While the feeder cell is not particularly limited, for example, fibroblasts (mouse embryonic fibroblast (MEF), mouse fibroblast (STO) and the like) can be mentioned. The feeder cell is preferably inactivated by a method known per se, for example, irradiation of radiation (gamma ray and the like), a treatment with an anti-cancer agent (mitomycin C and the like) and the like. Examples of the extracellular substrate component include fibrous protein such as gelatin, collagen, elastin and the like, glucosaminoglycan and proteoglycan such as hyaluronic acid, chondroitin sulfate and the like, cell adhesive protein such as fibronectin, vitronectin, laminin and the like, basal lamina component such as Matrigel and the like, and the like.

The floor plate cell differentiation inducing factor to be used in the differentiation method is not particularly limited as long as it is a substance that induces differentiation into a floor plate cell, and any substance known as a floor plate cell differentiation inducing factor can be used. The substance includes low-molecular-weight compound, peptide, protein and the like. Examples of the floor plate cell differentiation inducing factor include BMP inhibitors such as Noggin, LDN-193189 (4-(6-(4-(piperazin-1-yl)phenyl)pyrazolo[1,5-a]pyrimidin-3-yl)quinoline hydrochloride), dorsomorphin(6-[4-(2-piperidin-1-ylethoxy)phenyl]-3-pyridin-4-ylpyrazolo[1,5-a]pyrimidine) and the like; TGFβ family inhibitors such as SB431542 (4-[4-(1,3-benzodioxol-5-yl)-5-(2-pyridinyl)-1H-imidazol-2-yl]-benzamide), A-83-01 (3-(6-methylpyridin-2-yl)-1-phenylthiocarbamoyl-4-quinolin-4-ylpyrazole) and the like; GSK3β inhibitors such as CHIR99021 (6-[[2-[[4-(2,4-dichlorophenyl)-5-(5-methyl-1H-imidazol-2-yl)-2-pyrimidinyl]amino]ethyl]amino]-3-pyridinecarbonitrile), BIO (6-bromo-indirubin-3'-oxime) and the like; Smoothened agonists such as purmorphamine (N-(4-morpholinophenyl)-2-(1-naphthyloxy)-9-cyclohexyl-9H-purin-6-amine), SAG (N-methyl-N'-(3-pyridinylbenzyl)-N'-(3-chlorobenzo[b]thiophene-2-carbonyl)-1,4-diaminocyclohexane) and the like; and growth factors such as Sonic hedgehog (SHH), fibroblast growth factor-8 (FGF8)

and the like. These can be purchased from Axon Medchem BV, Wako Pure Chemical Industries, Ltd., Enzo Life Sciences, Inc., Merck Bioscience, Tocris bioscience, Stemgent, Inc, Sigma, R&D, PeproTech, Inc. and the like, and the same name or the same trade name indicates the same substance, and the structure and property are equal irrespective of the manufacturers. Even when they are not commercially available as products, those of ordinary skill in the art can also prepare them according to known documents.

The present inventors have found that differentiation of a stem cell into a floor plate cell can be more efficiently induced by this differentiation method by performing primary culture for 3-5 days in a medium containing LDN193189, SB431542, purmorphamine and CHIR99021 (SHH is optionally contained), followed by secondary culture in a medium containing LDN193189 and CHIR99021 for 5-8 days.

Therefore, a stem cell can be efficiently induced to differentiate into a floor plate cell by a combined use of LDN193189, SB431542, purmorphamine and CHIR99021 as the above-mentioned floor plate cell differentiation inducing factor, even without addition of a protein component such as SHH and the like to the medium, and a floor plate cell, and further, a dopaminergic neuron, can be produced at a lower cost than before.

While the concentration of the floor plate cell differentiation inducing factor in the medium in this differentiation method is appropriately determined according to the kind of the factor to be used, for example, the concentration of LDN193189, purmorphamine and CHIR99021 when they are used as a floor plate cell differentiation inducing factor is generally 0.05-10 μM, preferably 0.1-5 μM, for each of them. The concentration when SB431542 is used as a floor plate cell differentiation inducing factor is generally 1-20 μM, preferably 5-15 μM. The concentration when SHH is used as a floor plate cell differentiation inducing factor is generally 10-500 ng/ml, preferably 100-300 ng/ml.

A medium to be used for this differentiation method is not particularly limited as long as the above-mentioned floor plate cell differentiation inducing factor is contained and it is generally a medium used for culture of stem cell (hereinafter sometimes to be also referred to as a basal medium) added with a floor plate cell differentiation inducing factor.

The above-mentioned basal medium is not particularly limited as long as it can be used for culture of animal cells, such as NEUROBASAL medium, NEUROBASAL-A medium, Neural Progenitor Basal medium, NS-A medium, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, DMEM/F12 medium, ham medium, RPMI 1640 medium, Fischer's medium, and mixed medium thereof and the like. These basal media can be purchased from Invitrogen, SIGMA, Wako Pure Chemical Industries, Ltd., Sumitomo Dainippon Pharma Co., Ltd. and the like, and the same name or the same trade name of a medium indicates the same medium composition irrespective of the manufacturers. Since differentiation induction into a floor plate cell can be more efficiently performed, DMEM/F12 medium, NEUROBASAL medium, and a mixed medium thereof are preferably used as the basal medium.

The medium to be used in this differentiation method may be a serum-containing medium or a serum-free medium. As used herein, the serum-free medium means a basal medium free of a non-adjusted or unpurified serum, and a medium containing purified blood-derived components and animal tissue-derived components (e.g., growth factor) corresponds to a serum-free medium. When the medium to be used in this differentiation method is a serum-containing medium, and a serum of a mammal such as fetal bovine serum and the like can be used as the serum. The concentration of the serum in the medium is generally 0.01-20 wt %, preferably 0.1-10 wt %.

The medium to be used in this differentiation method may also contain a serum replacement. Examples of the serum replacement include albumin (e.g., lipid-rich albumin), transferrin, fatty acid, collagen precursor, trace element (e.g., zinc, selenium), B-27 supplement, N2 supplement, Replacement KnockOut serum replacement, 2-mercaptoethanol, 3'thiolglycerol, and equivalents thereof. The concentration of these in the media is the same as the concentration of the aforementioned serum in the medium.

In this differentiation method, N2 supplement and B-27 supplement (Brewer G. J. et al., J. Neurosci. Res. (1993) 35, 567) are preferably added to the medium as a serum replacement.

This Brewer reference lists the following compositions for the NEUROBASAL™ medium, the B27™ medium supplement, and the N2 medium supplement:

| THE NEUROBASAL™ MEDIUM FORMULATION | | |
|---|---|---|
| NEUROBASAL Medium Ingredients | Concentration (mg/L) | μM |
| Amino Acids | | |
| L-Alanine | 2.0 | 20 |
| L-Arginine hydrochloride | 84 | 400 |
| L-Asparagine-H$_2$O | 0.83 | 5 |
| L-Cysteine | 1.21 | 10 |
| Glycine | 30 | 400 |
| L-Histidine hydrochloride-H$_2$O | 42 | 200 |
| L-Isoleucine | 105 | 800 |
| L-Leucine | 105 | 800 |
| L-Lysine hydrochloride | 146 | 5 |
| L-Methionine | 300 | 200 |
| L-Phenylalanine | 66 | 400 |
| L-Proline | 7.76 | 67 |
| L-Serine | 42 | 400 |
| L-Threonine | 95 | 800 |
| L-Tryptophan | 16 | 80 |
| L-Tyrosine | 72 | 400 |
| L-Valine | 94 | 800 |
| Vitamins | | |
| D-calcium pantothenate | 4 | 8 |
| Choline chloride | 4 | 28 |
| Folic Acid | 4 | 8 |
| i-Inositol | 7.2 | 40 |
| Niacinamide | 4 | 30 |
| Pyridoxal hydrochloride | 4 | 20 |
| Riboflavin | 0.4 | 1 |
| Thiamine hydrochloride | 4 | 10 |
| Vitamin B12 | 0.34 | 0.2 |
| Inorganic Salts | | |
| Calcium Chloride (CaCl$_2$) (anhyd.) | 200.0 | 1,800 |
| Ferric Nitrate (Fe(NO$_3$)$_3$•9H$_2$O) | 0.1 | 0.2 |
| Potassium Chloride (KCl) | 400 | 5,360 |
| Magnesium Chloride (MgCl$_2$ anhydrous) | 77.3 | 812 |
| Sodium Bicarbonate (NaHCO$_3$) | 2200 | 26,000 |
| Sodium Chloride (NaCl) | 3000 | 51,300 |
| Sodium Phosphate monobasic (NaH$_2$PO$_4$—H$_2$O) | 125 | 900 |

-continued

THE NEUROBASAL™ MEDIUM FORMULATION

| NEUROBASAL Medium Ingredients | Concentration (mg/L) | μM |
|---|---|---|
| Other Components | | |
| D-Glucose | 4500 | 25,000 |
| HEPES | 2600 | 10,000 |
| Phenol Red | 8.1 | 23 |
| Sodium Pyruvate | 25 | 230 |

The NEUROBASAL medium, or any other medium with this formulation, is defined for purposes of this application as a "Base Medium."

The B27™ Medium Supplement Formulation

| B27 Medium Supplement Ingredients |
|---|
| Biotin |
| L-Carnitine |
| Corticosterone |
| Ethanolamine |
| D(+)-Galactose |
| Glutathione (reduced) |
| Linoleic Acid |
| Linolenic Acid |
| Progesterone |
| Putrescine |
| Retinyl acetate |
| Selenium |
| T3 triodo-l-thyronine) |
| DL-α-tocopherol (vitamin E) |
| DL-α-tocopherol acetate |
| Proteins |
| Albumin bovine |
| Catalase |
| Insulin |
| Superoxide dismutase |
| Transferrin |

The B27 medium supplement, or any other medium supplement with this formulation, is defined for purposes of this application as a "Medium Supplement A."

The N2 Medium Supplement Formulation

| N2 Medium Supplement Ingredients |
|---|
| Insulin |
| Transferrin |
| Selenium |

The N2 medium supplement, or any other medium supplement with this formulation, is defined for purposes of this application as a "Medium Supplement B."

In this case, the concentration of the N2 supplement in the medium is preferably 0.1-10 wt %, more preferably 0.5-2 wt %, and the concentration of the B-27 supplement is preferably 0.1-10 wt %, more preferably 1-5 wt %.

The KnockOut serum replacement can be purchased from Invitrogen. Other serum replacements can be purchased from Invitrogen, SIGMA, Wako Pure Chemical Industries, Ltd., Sumitomo Dainippon Pharma Co., Ltd. and the like, and the same name or the same trade name of a reagent or additive indicates the same composition irrespective of the manufacturers.

The medium to be used in this differentiation method may also contain lipid, amino acid (e.g., non-essential amino acid), vitamin, growth factor, cytokine, antioxidant, 2-mercaptoethanol, pyruvic acid, buffering agent, inorganic salt, antibiotic (e.g., penicillin and streptomycin) or antibacterial agent (e.g., amphotericin B) and the like. The concentration of these in the media is the same as the concentration of the aforementioned serum in the medium.

Other culture conditions such as culture temperature, $CO_2$ concentration and the like can be appropriately determined. While the culture temperature is not particularly limited, it is, for example, about 30-40° C., preferably about 37° C. The $CO_2$ concentration is, for example, about 1-10%, preferably about 5%.

In this differentiation method, differentiation of a stem cell into a floor plate cell can be confirmed by evaluating the expression variation of proteins and genes that are specifically expressed by the floor plate cell (in the present specification, the above-mentioned proteins and genes are sometimes referred to as a floor plate cell marker). The above-mentioned evaluation of expression variation of floor plate cell marker can be performed by, for example, an evaluation method of expression of protein by utilizing an antigen-antibody reaction, an evaluation method of gene expression by utilizing quantitative RT-PCR, and the like. Examples of the above-mentioned floor plate cell marker, which is differentiated into midbrain, include FOXA2 and LMX1A gene/protein.

1-2. Method of Producing Dopaminergic Neuron from Neural Progenitor Cell (the Production Method of the Present Invention)

The neural progenitor cells such as floor plate cell obtained by the above-mentioned differentiation method, and the like, can be further differentiated into a dopaminergic neuron by a step of culturing in a medium containing (i) a cAMP analogue and (ii) a MEK inhibitor. When a floor plate cell is used as a neural progenitor cell, addition of neurotrophic factors such as brain-derived neurotrophic factor (BDNF), glial cell line-derived neurotrophic factor (GDNF) and the like to a medium, which is generally used for differentiation induction from a floor plate cell into a dopaminergic neuron, is not essential in the production method of the present invention.

The cAMP analogue to be used in the production method of the present invention is not particularly limited as long as it is a compound having a structure similar to that of cAMP and capable of elevating intracellular cAMP concentration on contact with the cell.

Examples of the above-mentioned cAMP analogue include 8-bromo-cAMP, dibutyryl-cAMP, N6-benzoyl-cAMP, 8-thiomethyl-cAMP and the like. These can be purchased from Sigma, Merck Bioscience, Wako Pure Chemical Industries, Ltd. and the like, and the same name or the same trade name indicates the same substance and the structure and property are equal irrespective of the manufacturers. Even when they are not commercially available as products, those of ordinary skill in the art can also prepare them according to known documents.

As the cAMP analogue to be used in the production method of the present invention, dibutyryl-cAMP is preferable.

While the concentration of the cAMP analogue in the medium is appropriately determined according to the kind of the cAMP analogue to be used, the concentration of dibutyryl-cAMP as a cAMP analogue is generally 0.01-5 mM, preferably 0.1-1 mM.

The MEK inhibitor to be used in the production method of the present invention refers to a substance having a MAP kinase (Mitogen activated protein kinase/ERK Kinase;

MEK) inhibitory activity, and an inhibitor of the upstream factor of MEK signal transduction pathway (e.g., FGF receptor inhibitor) is also included in the MEK inhibitor of the present invention as long as it inhibits the activity of MEK.

Examples of the above-mentioned MEK inhibitor include PD0325901 (N-[(2R)-2,3-dihydroxypropoxy]-3,4-difluoro-2-[(2-fluoro-4-iodophenyl)amino]-benzamide), PD184352 (2-(2-chloro-4-iodophenylamino)-N-cyclopropylmethoxy-3,4-difluorobenzamide), SU5402 (3-[4-methyl-2-(2-oxo-1,2-dihydro-indol-3-ylidenemethyl)-1H-pyrrol-3-yl]-propanoic acid), PD173074 (N-[2-[[4-(diethylamino)butyl]amino-6-(3,5-dimethoxyphenyl)pyrido[2,3-d]pyrimidin-7-yl]-N'-(1,1-dimethyl)urea) and the like. These can be purchased from Axon Medchem BV, Wako Pure Chemical Industries, Ltd., Enzo Life Sciences, Inc., Merck Bioscience, Tocris bioscience, Stemgent, Sigma and the like, and the same name or the same trade name indicates the same substance and the structure and property are equal irrespective of the manufacturers. Even when they are not commercially available as products, those of ordinary skill in the art can also prepare them according to known documents.

In addition, antisense oligonucleotide, siRNA and the like for MEK mRNA can also be used as a MEK inhibitor. They are commercially available or can be synthesized according to previous reports.

As the MEK inhibitor to be used in the production method of the present invention, PD0325901, PD184352 or SU5402 is preferable.

While the concentration of the MEK inhibitor in the medium is appropriately determined according to the kind of the MEK inhibitor to be used, the concentration of PD0325901 or PD184352 used as a MEK inhibitor is generally 0.1-10 µM, preferably 1-5 µM. The concentration of SU5402 used as a MEK inhibitor is generally 0.1-20 µM, preferably 5-15 µM.

In the production method of the present invention, cAMP analogue and MEK inhibitor may be simultaneously added to the medium, or added to the medium in a staggered manner as long as they can induce differentiation from neural progenitor cells into a dopaminergic neuron. The cAMP analogue and the MEK inhibitor are conveniently and preferably added simultaneously to the medium.

The medium to be used in the production method of the present invention is produced by adding a cAMP analogue and a MEK inhibitor to the basal medium exemplified as the differentiation method of the above-mentioned 1-1. (optionally containing various additives exemplified above, serum or serum replacement when desired).

The medium to be used in the production method of the present invention may be produced using a basal medium of the same kind as the basal medium used for the aforementioned production method of the floor plate cell, or produced using a different kind of the basal medium. However, it is preferably produced using the same kind of the basal medium.

A high-quality dopaminergic neuron can be produced more efficiently by adding, in addition to the above-mentioned cAMP analogue and MEK inhibitor, ascorbic acid or a salt thereof to the medium to be used in the production method of the present invention.

Examples of the ascorbic acid salt usable in the production method of the present invention include, but are not limited to, sodium ascorbate, potassium ascorbate, calcium ascorbate and the like.

The concentration of ascorbic acid or a salt thereof to be added to the medium is generally 0.01-10 mM, preferably 0.05-1 mM.

Ascorbic acid or a salt thereof may be added to the medium simultaneously with the cAMP analogue and MEK inhibitor, or may be added separately to the medium in a staggered manner as long as differentiation from neural progenitor cells into a dopaminergic neuron can be induced. Ascorbic acid or a salt thereof is conveniently and preferably added to the medium simultaneously with the cAMP analogue and MEK inhibitor.

In the production method of the present invention, a high-quality dopaminergic neuron can be produced more efficiently by culturing neural progenitor cells in the medium added with an activator of activin receptor-like kinase-4,7 in addition to the above-mentioned cAMP analogue and MEK inhibitor, as well as the period of differentiation induction into a dopaminergic neuron can also be shortened. While the activator of activin receptor-like kinase-4,7 is not particularly limited as long as it activates activin receptor-like kinase-4 and/or activin receptor-like kinase-7, for example, nodal, GDF-1, Vg1, activin and the like can be mentioned. Preferred is activin (particularly, activin A).

Activin is a 241W peptidic cell proliferation and differentiation factor belonging to the TGFβ (transforming growth factor β) family, wherein two β subunits constitute a dimer via an SS bond (Ling, N., et al., (1986) Nature 321, 779-782; Vale, W., et al., (1986) Nature 321, 776-779). Activin is known to include activin A, B, C, D and AB. In the production method of the present invention, any of activin A, B, C, D, AB can be used. When activin is used in the production method of the present invention, activin A is particularly preferably used as activin. As the activin, activin derived from any mammal such as human, mouse and the like can be used. When activin is used in the production method of the present invention, activin derived from the same animal species as the neural progenitor cell to be used is preferably used. For example, when a neural progenitor cell derived from human is used as the starting material, activin derived from human is preferably used. These activins are commercially available.

While the concentration of activin in the medium in the production method of the present invention is appropriately determined according to the kind of activin to be used, the concentration of activin A used as activin is generally 0.1-200 ng/ml, preferably 5-150 ng/ml, particularly preferably 10-100 ng/ml.

Activin may be added to the medium simultaneously with the cAMP analogue and MEK inhibitor, or may be added separately to the medium in a staggered manner as long as differentiation from neural progenitor cells into a dopaminergic neuron can be induced. Activin is conveniently and preferably added to the medium simultaneously with the cAMP analogue and MEK inhibitor.

The production method of the present invention is performed by culturing in a $CO_2$ incubator aerated with 1-10% (preferably 5%) carbon dioxide at a culture temperature (generally 30-40° C., preferably about 37° C.) suitable for culturing neural progenitor cells.

In the production method of the present invention, differentiation of neural progenitor cells into a dopaminergic neuron can be confirmed by evaluating the expression variation of proteins and genes that are specifically expressed by the dopaminergic neuron (in the present specification, the above-mentioned proteins and genes are sometimes referred to as a dopaminergic neuron marker). The above-mentioned evaluation of expression variation of dopaminergic neuron cell marker can be performed by, for example, an evaluation method of expression of protein by utilizing an antigen-antibody reaction, an evaluation method of gene expression by utilizing quantitative RT-PCR and the like. Examples of the above-mentioned dopaminergic neuron cell marker, which is present in the midbrain, include tyrosine hydroxylase (TH), FOXA2, LMX1A, and NURR1 gene/protein.

In addition, whether the dopaminergic neuron obtained by the production method of the present invention has functions equivalent to those of dopaminergic neuron in vivo can be confirmed by evaluating dopamine release, and responsiveness to oxidative stress and drug stimulation.

Using the production method of the present invention, a high-quality dopaminergic neuron can also be efficiently produced using, as a starting material, a floor plate cell or neural progenitor cell other than the floor plate cell obtained by the differentiation method of the above-mentioned 1-1.

In the production method of the present invention, a high-quality dopaminergic neuron can be produced in a large amount by efficiently inducing differentiation of neural progenitor cells into a dopaminergic neuron. Since the dopaminergic neuron has phenotypic characteristics and functions similar to those of dopaminergic neurons in vivo, it can achieve a high engrafted rate when used as a medicament in a cell transplantation therapy for treating a disease caused by decreased production (release) of dopamine, for example, neurodegenerative diseases such as Parkinson's disease and the like. In addition, it is useful as a tool for developing a therapeutic drug for the disease.

The cells obtained during the processes of the production method of the present invention and the dopaminergic neuron of the present invention can be cryopreserved and thawed. Freezing and thawing methods of cells are known in the pertinent field, and are not particularly limited as long as they do not influence differentiation potency, viability, dopamine production capability and the like of the cells. For example, the dopaminergic neuron of the present invention can be preserved at −80° C. by washing cells with PBS, detaching same from a culture dish with a cell-dispersion solution (e.g., Accutase (registered trade mark) Innovative Cell Technologies), removing the cell-dispersion solution, and suspending the cells in a cryopreservation solution (e.g., cell banker 2 (LSI Medience Corporation)). Examples of the thawing method include a method comprising thawing in a thermostatic tank at 37° C., washing a cryopreservation solution by centrifugation, and suspending in a medium for use, and the like. When the cells obtained during the processes of the production method of the present invention are frozen and thawed, Nurr1 positive dopaminergic neuron can also be induced from the cells after thawing.

2. Medicament Containing Dopaminergic Neuron

The present invention provides a medicament containing a dopaminergic neuron produced by the above-mentioned production method of the present invention (sometimes to be abbreviated as the medicament of the present invention in the present specification).

As used herein, the dopaminergic neuron is not particularly limited as long as it is a cell obtained by the above-mentioned production method of the present invention.

In this medicament, a dopaminergic neuron is used as is, or as a cell aggregate obtained by concentration by passing through a filter and the like, such as pellet and the like, and the like. Furthermore, the medicament can also be added with a protector such as DMSO (dimethyl sulfoxide) and the like and cryopreserved. For safer utilization of the medicament, the medicament may be subjected to a treatment under such conditions as to retain the functions as a dopaminergic neuron and denature pathogenic protein, for example, heat treatment, radiation treatment and the like. Moreover, to prevent growth of dopaminergic neuron in an amount more than necessary, the medicament may be subjected to, in combination with the above-mentioned treatments, suppression of growth by a mitomycin C pre-treatment and the like, and a treatment by a method including introducing a gene of a metabolic enzyme naturally absent in mammals into the neurons, administering an agent in an unactivated form as necessary to allow for the agent to be converted to a toxicant only in the neurons, into which the gene of a metabolic enzyme naturally absent in mammals has been introduced, thus leading the cells to eradication (suicide gene therapy) and the like.

Since the medicament of the present invention is safe and has low toxicity, it can be administered to a mammal (e.g., human, mouse, rat, guinea pig, swine, monkey).

As the form of administration (transplantation method) of the medicament of the present invention to human, a method described in Nature Neuroscience, 2, 1137 (1999) or N Engl J Med.; 344: 710-9 (2001) can be mentioned. Preferably, the medicament of the present invention is administered (transplanted) to a dopamine deficient region in the brain.

A dopaminergic neuron prepared using patient's own cell or a cell of a donor having a histocompatibility type in a tolerable range is preferably used for the medicament of the present invention. When sufficient cells cannot be obtained due to age, constitution and the like, the cells embedded with a polyethylene glycol or silicon capsule, a porous container and the like can also be transplanted to avoid rejection. The dose (amount to be transplanted) and administration frequency (number of times to be transplanted) of the medicament of the present invention can be appropriately determined according to the age, body weight, symptom and the like of the patients who receive administration.

A medicament containing the dopaminergic neuron of the present invention can efficiently engraft in the body of patients by administration (transplantation) thereof, which in turn enables efficient production (release) of dopamine in the body of patients. Therefore, the medicament of the present invention is useful for the treatment of diseases caused by decreased production (release) of dopamine, for example, neurodegenerative diseases such as Parkinson's disease, Huntington chorea, Alzheimer's disease, epilepsy and schizophrenia and the like.

3. Other Use

Since the dopaminergic neuron of the present invention has phenotypic characteristics and functions similar to those of dopaminergic neuron in vivo, it is useful for screening for a drug compound, preferably a compound for the treatment of neurodegenerative diseases. For example, whether the test compound is useful as a medicament can be evaluated by adding the test compound alone or in combination with other medicament to the dopaminergic neuron of the present invention, and measuring morphological or functional change of the neuron. Examples of the method for measuring the functional change include measuring the amount of dopamine produced or released from the neuron. As used herein, the dopaminergic neuron is preferably a cell showing the same phenotype as the disease to be the treatment target, and particularly preferred is a dopaminergic neuron produced by inducing differentiation of a stem cell produced from a somatic cell derived from the disease.

Examples of the test compound include peptide, protein, antibody, nonpeptidic compound, synthetic compound, fermentation product, cell extract, plant extract, animal tissue extract, plasma and the like. As used herein, the test compound may form a salt. As the salt, a salt with a physiologically acceptable acid (e.g., inorganic acid, organic acid), a base (e.g., alkali metal salt, alkaline earth metal salt, aluminum salt) and the like is used, and examples of such salt include a salt with an inorganic acid (e.g., hydrochloric acid, phosphoric acid, hydrobromic acid, sulfuric acid), a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), sodium salt, potassium salt, calcium salt, magnesium salt, barium salt, and aluminum salt can be used.

The medicament obtained using the above-mentioned screening can be formulated using a physiologically acceptable additive and according to a known method.

Examples of the dosage form of the thus-obtained preparation include oral preparations such as tablet applied with sugar coating as necessary, capsule, elixir, microcapsule and the like; and parenteral agents such as injection and the like. The content of the active ingredient (compound selected by the above-mentioned screening method) in the preparation is, for example, 0.1-90 wt %.

Examples of the aforementioned additive include binders such as gelatin, cornstarch, tragacanth, gum arabic and the like; excipients such as crystallinity cellulose and the like; swelling agents such as cornstarch, gelatin, alginic acid and the like; lubricants such as such as magnesium stearate and the like; sweetening agents such as sucrose, lactose, saccharin and the like; flavors such as peppermint, *Gaultheria adenothrix* oil, cherry and the like; liquid carriers such as fats and oils, water for injection, vegetable oil (e.g., sesame oil, coconut oil, soybean oil), buffering agent (e.g., phosphate buffer, sodium acetate buffer) and the like; solubilizing agents (e.g., ethanol, propylene glycol, polyethylene glycol); non-ionic surfactants (e.g., polysorbate80™, HCO-50); solubilizing agents (e.g., benzyl benzoate, benzyl alcohol); soothing agents (e.g., benzalkonium chloride, procaine hydrochloride); stabilizers (e.g., human serum albumin, polyethylene glycol); preservatives (e.g., benzyl alcohol, phenol); and antioxidants.

Examples of the aforementioned water for injection include saline; and isotonic solutions containing glucose, D-sorbitol, D-mannitol, sodium chloride and the like.

Since a medicament (preferably, a therapeutic drug for neurodegenerative disease) obtained by the above-mentioned screening is safe and low toxic, it can be administered orally or parenterally to, for example, mammals (e.g., human, mouse, rat, rabbit, sheep, swine, bovine, horse, cat, dog, monkey, chimpanzee).

The dose and administration frequency of the medicament can be appropriately determined according to the action thereof, target disease, administration subject, administration route and the like.

The dopaminergic neuron of the present invention can also be used for the toxicity evaluation of a compound. For example, whether the test compound has toxicity can be evaluated by adding the test compound alone or in combination with other medicament to the dopaminergic neuron of the present invention, and measuring morphological or functional change of the neuron. Examples of the method for measuring the functional change include measuring the amount of dopamine produced or released from the neuron. Examples of the test compound include peptide, protein, antibody, nonpeptidic compound, synthetic compound, fermentation product, cell extract, plant extract, animal tissue extract, and plasma. The test compound here may form a salt such as those described in the above-mentioned screening.

The dopaminergic neuron obtained by the production method of the present invention can also be used for verification of drug discovery target and analysis of disease mechanism and the like.

In another embodiment, the present invention also provides a reagent and a kit for producing a dopaminergic neuron from neural progenitor cells, which contains (i) a cAMP analogue and (ii) a MEK inhibitor.

The above-mentioned reagent and kit may further contain (1) ascorbic acid or a salt thereof and/or (2) an activator of activin receptor-like kinase-4,7.

As the above-mentioned cAMP analogue, MEK inhibitor and activator of activin receptor-like kinase-4,7, those usable for the production method of the present invention can be mentioned.

The contents disclosed in any publication cited in the present specification, including patents and patent applications, are hereby incorporated in their entireties by reference, to the extent that they have been disclosed herein.

While the present invention is explained in more detail in the following by referring to Examples, the present invention is not limited in any way by the Examples shown below.

EXAMPLES

Reference Example 1

Maintenance and Culture of Undifferentiated Human iPS Cell

As human iPS cell, 253G1 strain (Nature Biotechnology 2008; 26: 101-106) or 201B7 strain (Cell. 2007; 131: 861-872) was used.

The iPS cells (253G1 strain or 201B7 strain) in an undifferentiated state were maintained and cultured in two ways by (i) a method using a feeder cell and (ii) a method without using a feeder cell.

(i) Method Using a Feeder Cell

As a feeder cell, mouse fibroblasts (MEFs, KITAYAMA LABES Co., Ltd.) which underwent a mitomycin C (Wako Pure Chemical Industries, Ltd.) treatment to inactivate the growth thereof and were seeded on a gelatin-coated plate were used. In this method, a medium for primate ES cell (ReproCELL Incorporated) added with 4 ng/ml bFGF (basic fibroblast growth factor) (PeproTech) and 0.5×Penicillin-streptomycin (Wako Pure Chemical Industries, Ltd.) was used as a medium, and the cells were cultured at 37° C. under 5% $CO_2$. The medium was exchanged every day, and the cells were passaged every 6-7 days. For the above-mentioned passage, iPS cells in the form of a cell aggregate were detached from the plate by using a cell detachment solution for primate ES cell (manufactured by Reprocell Inc.), and the detached iPS cells were seeded on new feeder cells.

(ii) Method without Using a Feeder Cell

In the method without using a feeder cell, a vitronectin (Life Technologies)-coated plate was used. In this method, Essential 8 (Life Technologies) added with 0.5×Penicillin-streptomycin (Wako Pure Chemical Industries, Ltd.) was used as a medium, and the cells were cultured at 37° C. under 5% $CO_2$. The medium was exchanged every day, and the cells were passaged every 6-7 days. For the above-mentioned passage, iPS cells in the form of a cell aggregate were detached from the plate by using PBS added with 0.5 mM EDTA, and the detached iPS cells were seeded on a new plate coated with vitronectin.

Reference Example 2

Preculture of Human iPS Cell

For preculture of differentiation induction into a floor plate cell, undifferentiated human iPS cells maintained by culturing by the method (i) or (ii) described in the above-mentioned Reference Example 1 were seeded in a 96 well plate.
(i) When iPS Cells Maintained on Feeder Cells are Used iPS cells maintained in the form of a cell aggregate were treated for 10 sec with a cell detachment solution for primate ES cell, and gently pipetted to remove MEFs to some extent. Then, the cells were washed with PBS, treated with Accutase (Innovative Cell Technologies) at 37° C. for 5 min, and dissociated until single cells were obtained. Then, the iPS cells dispersed in a medium were seeded in a 96 well plate at a density of $1.5-2\times10^4$ cells per well, and cultured (precultured) at 37° C. under 5% $CO_2$ for one day. As the culture medium used for seeding, a medium for primate ES cell added with 10 μM Y27632 ((R)-(+)-trans-4-(1-amino-ethyl)-N-(4-pyridyl)cyclohexanecarboxamide) (Wako Pure Chemical Industries, Ltd.) was used.
(ii) When iPS Cells Maintained without Using Feeder Cells are Used iPS cells maintained in the form of a cell aggregate were treated for 10 min with PBS added with 0.5 mM EDTA, and dissociated until single cells were obtained. Then, the iPS cells dispersed in a medium were seeded in a 96 well plate at a density of $1.5-2\times10^4$ cells per well, and cultured (precultured) at 37° C. under 5% $CO_2$ for one day. As the culture medium used for seeding, Essential 8 added with 10 μM Y27632 (Wako Pure Chemical Industries, Ltd.) was used. As the above-mentioned 96 well plate, one coated at 37° C. overnight with Matrigel (BD) 1/30-1/40 diluted with DMEM/F12 (Life Technologies Corporation) was used.

Reference Example 3

Differentiation Induction from Human iPS Cell into Floor Plate Cell

Differentiation of human iPS cell into floor plate cell was induced by the following method.

The medium after preculture as described in the above-mentioned Reference Example 2 was exchanged with a differentiation induction medium containing factors inducing differentiation into floor plate cell (LDN193189 (0.5 μM, Axon MedChem B.V.), SB431542 (10 μM, Wako Pure Chemical Industries, Ltd.), purmorphamine (0.5 μM, Merck), SHH (200 ng/ml, R&D systems) and CHIR99021 (1 μM, Axon MedChem)) (day 0 of culture), and the cells were cultured at 37° C. under 5% $CO_2$ for 5 days. Then, the medium was exchanged with a differentiation induction medium containing 0.5 μM LDN193189 and 1 μM CHIR99021, and the cells were cultured at 37° C. under 5% $CO_2$ for 5-8 days (total 10-13 days). Here, as the above-mentioned differentiation induction medium, (a) NEUROBASAL (Life Technologies) containing 2% B27 (Life Technologies corporation) and 2 mM GlutaMax I (Life Technologies corporation) (hereinafter to be indicated as Neuro/B27), or (b) DMEM/F12 containing 1% N2 (Wako Pure Chemical Industries, Ltd.) and 2% B27 (Life Technologies corporation) (hereinafter to be indicated as N2B27) was used. The medium was exchanged every 3-4 days during these culture periods.

The Neurobasal™ medium, from Life Technologies (now part of ThermoFischer Scientific), has the following ingredients, as listed on the ThermoFischer website:

| NEUROBASAL COMPONENT | CONCENTRATION (mg/L) | mM |
|---|---|---|
| Amino Acids | | |
| Glycine | 30.0 | 0.4 |
| L-Alanine | 2.0 | 0.02247191 |
| L-Arginine hydrochloride | 84.0 | 0.39810428 |
| L-Asparagine-$H_2O$ | 0.83 | 0.0055333334 |
| L-Cysteine | 31.5 | 0.2603306 |
| L-Histidine hydrochloride-$H_2O$ | 42.0 | 0.2 |
| L-Isoleucine | 105.0 | 0.8015267 |
| L-Leucine | 105.0 | 0.8015267 |
| L-Lysine hydrochloride | 146.0 | 0.7978142 |
| L-Methionine | 30.0 | 0.20134228 |
| L-Phenylalanine | 66.0 | 0.4 |
| L-Proline | 7.76 | 0.06747826 |
| L-Serine | 42.0 | 0.4 |
| L-Threonine | 95.0 | 0.79831934 |
| L-Tryptophan | 16.0 | 0.078431375 |
| L-Tyrosine | 72.0 | 0.39779004 |
| L-Valine | 94.0 | 0.8034188 |
| Vitamins | | |
| Choline chloride | 4.0 | 0.028571429 |
| D-Calcium pantothenate | 4.0 | 0.008385744 |
| Folic Acid | 4.0 | 0.009070295 |
| Niacinamide | 4.0 | 0.032786883 |
| Pyridoxal hydrochloride | 4.0 | 0.019607844 |
| Riboflavin | 0.4 | 0.0010638298 |
| Thiamine hydrochloride | 4.0 | 0.011869436 |
| Vitamin B12 | 0.0068 | 5.0184503E−6 |
| i-Inositol | 7.2 | 0.04 |
| Inorganic Salts | | |
| Calcium Chloride ($CaCl_2$) (anhyd.) | 200.0 | 1.8018018 |
| Ferric Nitrate ($Fe(NO_3)_3 \cdot 9H_2O$) | 0.1 | 2.4752476E−4 |
| Magnesium Chloride (anhydrous) | 77.3 | 0.8136842 |
| Potassium Chloride (KCl) | 400.0 | 5.3333335 |
| Sodium Bicarbonate ($NaHCO_3$) | 2200.0 | 26.190475 |
| Sodium Chloride (NaCl) | 3000.0 | 51.724136 |
| Sodium Phosphate monobasic ($NaH_2PO_4$—$H_2O$) | 125.0 | 0.9057971 |
| Zinc sulfate ($ZnSO_4 \cdot 7H_2O$) | 0.194 | 6.736111E−4 |
| Other Components | | |
| D-Glucose (Dextrose) | 4500.0 | 25.0 |
| HEPES | 2600.0 | 10.92437 |
| Phenol Red | 8.1 | 0.021519661 |
| Sodium Pyruvate | 25.0 | 0.22727273 |

The Neurobasal medium, or any other medium with this formulation, is defined for purposes of this application as a "Base Medium."

The B27™ medium supplement, from Life Technologies/Scientific), has the following ingredients, as listed on the ThermoFischer website:

| B27 COMPONENT |
| --- |
| Vitamins |
| Biotin
DL Alpha Tocopherol Acetate
DL Alpha Tocopherol
Vitamin A (acetate) |
| Proteins |
| BSA, fatty acid free Fraction V
Catalase
Human Recombinant Insulin
Human Transferrin
Superoxide Dismutase |
| Other Components |
| Corticosterone
D-Galactose
Ethanolamine HCl
Glutathione (reduced)
L-Carnitine HCl
Linoleic Acid
Linolenic Acid
Progesterone
Putrescine•2HCl
Sodium Selenite
T3 (triodo-l-thyronine) |

The B27 medium supplement, or any other medium supplement with this formulation, is defined for purposes of this application as a "Medium Supplement A."

The N2 medium supplement, from Waco Pure Chemical Industries, has the following ingredients, as listed on the Waco Pure Chemical Industries website:

| N2 Medium Supplement Ingredient | Concentration (mg/L) |
| --- | --- |
| Insulin, human, recombination product | 500.00 |
| Transferrin, human origin | 10,000.00 |
| Progesterone | 0.63 |
| Putrescine dihydrochloride | 1,611.00 |
| Sodium selenite | 0.52 |

The N2 medium supplement, or any other medium supplement with this formulation, is defined for purposes of this application as a "Medium Supplement B."

To examine expression variation of floor plate cell marker due to the presence or absence of factors inducing differentiation into floor plate cell (LDN193189, SB431542, purmorphamine, SHH and CHIR99021), the cells on day 13 of culture were recovered, and total RNA fraction was purified using RNeasy (Qiagen). Using PrimeScript RT reagent kit (Takara Bio Inc.), cDNA was synthesized, quantitative RT-PCR was performed, and the gene expression levels of floor plate cell markers FOXA2 and LMX1A were measured. The results are shown in FIG. 1. When all 5 kinds of LDN193189, SB431542, SHH, purmorphamine and CHIR99021 were added (All in FIG. 1), both FOXA2 and LMX1A showed high expression. Thus, it was clarified that floor plate cell can be efficiently induced by adding all the above-mentioned 5 kinds. Even when SHH was excluded from the above-mentioned 5 kinds (−SHH in Figure), the expression of FOXA2 and LMX1A was elevated to a certain degree. Thus, it is considered that floor plate cell can be induced even when SHH is not used, namely, when nothing but those compounds are added as differentiation inducing factors. In addition, even when FGF8 widely used as a factor for inducing neuroectoderm differentiated from human ES/iPS cell into the direction of midbrain region was added in addition to the above-mentioned 5 kinds, the expression of FOXA2 and LMX1A scarcely changed (All+FGF8 in FIG. 1). Therefore, FGF8 is considered to be not essential for this system.

Figure 2:
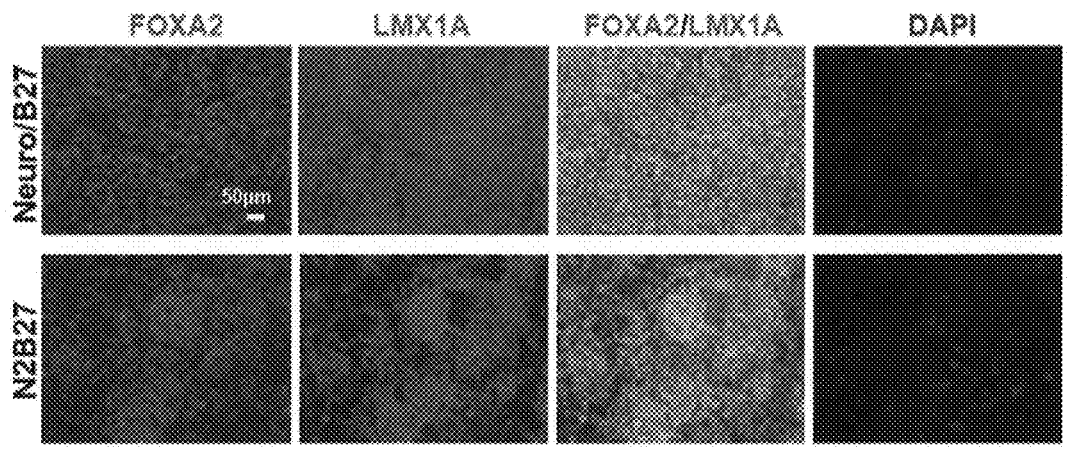
FIG. 2 shows the results of immunofluorescent staining of induced floor plate cells with anti-FOXA2 antibody and anti-LMX1A antibody on day 13 of culture. As the cell line, 253G1 strain was used. Red shows the nucleus of FOXA2 positive cells, green shows the nucleus of LMX1A positive cells, and blue (DAPI staining) shows the cell nucleus.

Then, to examine expression of FOXA2 and LMX1A proteins on day 13 of culture, immunofluorescent staining using anti-FOXA2 antibody and anti-LMX1A antibody was performed. The cells were cultured until day 13 by using all 5 kinds of LDN193189, SB431542, SHH, purmorphamine and CHIR99021, 4% para-formaldehyde (Wako Pure Chemical Industries, Ltd.) was added, and the cells were incubated at room temperature for 30 mM to fix the cells. The cells were reacted with anti-FOXA2 antibody (sc-6544, Santa Cruz Biotechnology, Inc.) and anti-LMX1A antibody (AB10533, Nihon Millipore K.K.) as the primary antibodies, and sequentially reacted with Alexa488-labeled secondary antibody (Invitrogen) and Alexa568-labeled secondary antibody, corresponding to the immunized animal of the primary antibody, as the secondary antibodies, and observed under a fluorescence microscope. The results are shown in FIG. 2. Even when any of the aforementioned (a) and (b) was used as a differentiation induction medium, most of the cells were observed to express both FOXA2 and LMX1A proteins.

From the above results, it was clarified that floor plate cell can be efficiently induced by culturing in a differentiation induction medium added with LDN193189, SB431542, SHH, purmorphamine and CHIR99021 for 5 days, and thereafter in a differentiation induction medium added with LDN193189 and CHIR99021 for 5-8 days.

Example 1

Induction of Differentiation from Floor Plate Cell into Dopaminergic Neuron

Floor plate cells were induced by a method similar to the methods described in Reference Examples 1 to 3, the medium was exchanged with (A) Neuro/B27 added with 3 factors of 0.1 mM ascorbic acid (SIGMA), 0.5 mM dibutyryl-cAMP (SIGMA, hereinafter to be indicated as dbcAMP) and 3 µM PD0325901, or (B) Neuro/B27 added with 2 factors of 0.1 mM ascorbic acid and 0.5 mM dbcAMP on day 13 of culture, and the cells were cultured at 37° C. under 5% CO$_2$ for not less than 30 days. The medium was exchanged every 3-4 days during the above-mentioned culture periods.

Experimental Example 1

Figure 3:
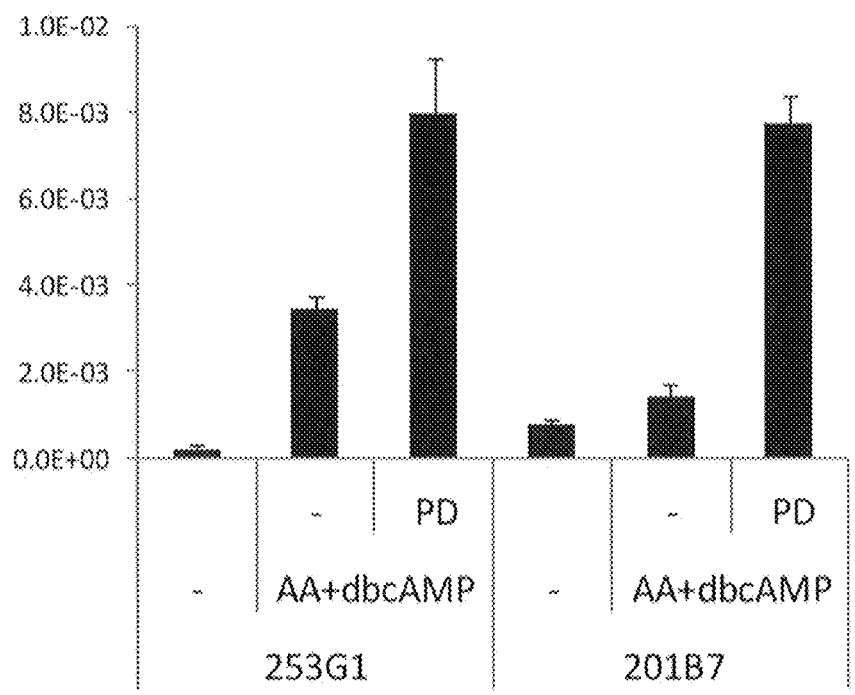
FIG. 3 shows the results of expression variation of NURR1, which were obtained by inducing differentiation of floor plate cells, culturing the cells by adding various combinations of ascorbic acid (AA), dibutyryl-cAMP (db-cAMP) and PD0325901 (PD) from 13 days after the induction, and examining the expression variation by quantitative RT-PCR on day 45. As the cell lines, 253G1 strain and 201B7 strain were used. The value of the Y axis shows the copy number of each gene normalized with the copy number of GAPDH, and the error bar shows standard deviation.

Analysis of expression of midbrain dopaminergic neuron marker gene and marker protein after dopaminergic neuron differentiation induction On day 45 of culture, the cells were recovered, and expression variation of NURR1 known as a transcription factor extremely important for the differentiation, maturation and maintenance of functions of midbrain dopaminergic neuron was examined. The results thereof are shown in FIG. 3. The expression of NURR1 was elevated by differentiation induction with the addition of 2 factors of ascorbic acid and dbcAMP, and the expression was further elevated highly by adding PD0325901 in addition to the two factors.

Figure 4:
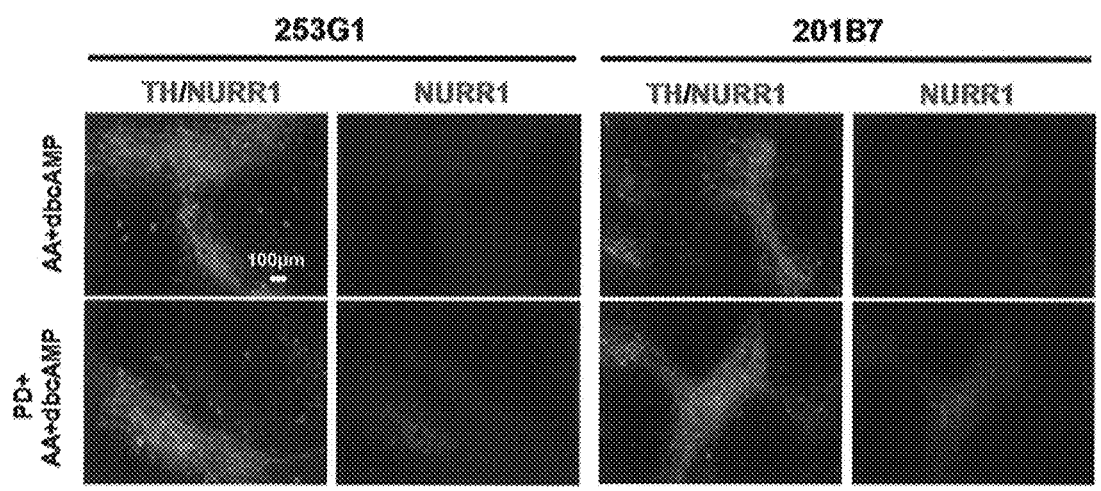
FIG. 4 shows the results of immunofluorescent staining using anti-TH antibody and anti-NURR1 antibody on day 45 of culture, after differentiation induction in the same manner as in FIG. 3. As the cell lines, 253G1 strain and 201B7 strain were used. Green shows the cell body of TH positive cells, and red shows the nucleus of NURR1 positive cells.
Figure 5:
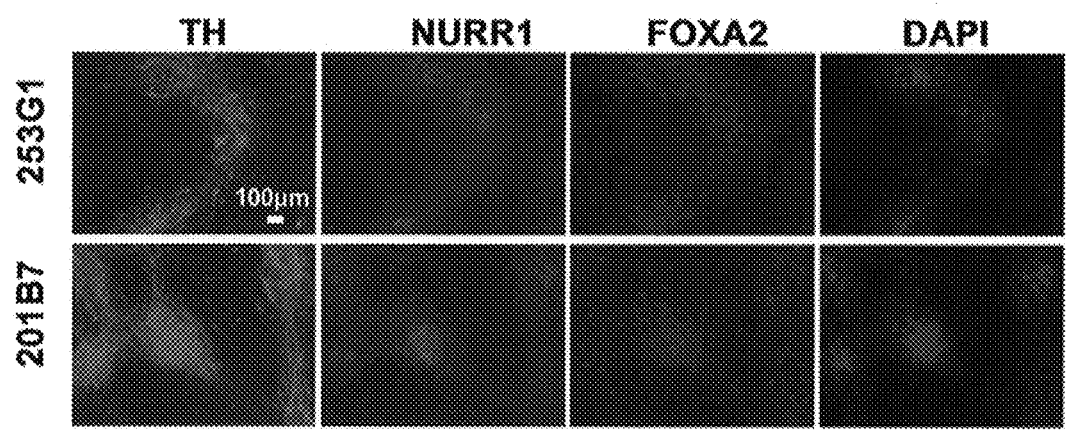
FIG. 5 shows the results of immunofluorescent staining, which were obtained by inducing differentiation of floor plate cells, culturing the cells by adding ascorbic acid (AA), dibutyryl-cAMP(dbcAMP) and PD0325901(PD) from 13 days after the induction, and performing immunofluorescent staining using anti-TH antibody, anti-NURR1 antibody and anti-FOXA2 antibody on day 45 (253G1 strain) or day 52 (201B7 strain). As the cell lines, 253G1 strain and 201B7 strain were used. Green shows the cell body of TH positive cells, red shows the nucleus of NURR1 positive cells, magenta shows the nucleus of FOXA2 positive cells, and blue (DAPI staining) shows the cell nucleus.
Figure 6:
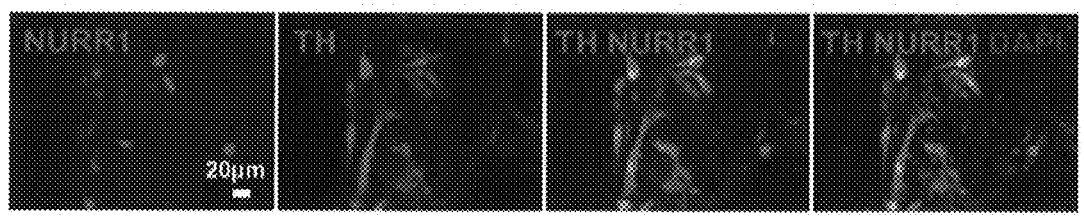
FIG. 6 shows observation of the results obtained using the 253G1 strain in FIG. 5 at high magnification. Green shows the cell body of TH positive cells, red shows the nucleus of NURR1 positive cells, and blue (DAPI staining) shows the cell nucleus.

Then, the expression of midbrain dopaminergic neuron markers TH, NURR1 and FOXA2 proteins was examined by immunofluorescent staining using anti-TH antibody, anti-NURR1 antibody and anti-FOXA2 antibody. Floor plate cells were induced by a method similar to the methods described in Reference Examples 1 to 3, differentiation induction was performed by exchanging the medium with (A) Neuro/B27 added with 3 factors of ascorbic acid, dbcAMP and PD0325901, or (B) Neuro/B27 added with 2 factors of ascorbic acid and dbcAMP from day 13 of culture, 4% PFA was added on days 45-52 of culture, and the cells were fixed at room temperature for 30 min. The cells were reacted with anti-TH antibody (AB152, Nihon Millipore K.K.), anti-NURR1 antibody (PP-N1404-00, Perseus Proteomics) and anti-FOXA2 antibody (sc-6544, Santa Cruz) as the primary antibodies, and sequentially reacted with Alexa488-labeled secondary antibody, Alexa568-labeled secondary antibody and Alexa647-labeled secondary antibody, corresponding to the immunized animal of the primary antibody, as the secondary antibodies, and observed under a fluorescence microscope. The results are shown in FIG. 4, FIG. 5 and FIG. 6. Under both conditions, the cells expressing TH protein are similarly observed, and staining with NURR1 protein clearly became strongly-positive by the addition of PD0325901 (Example 1, (A)) (FIG. 4), and many cells simultaneously expressing TH, NURR1 and FOXA2 proteins were observed (FIG. 5). FIG. 6 shows stained images when observed at high magnification. The above results were almost similarly obtained with 253G1 and 201B7 strains.

Therefrom it was clarified that a midbrain dopaminergic neuron can be induced several dozen times more efficiently by inducing differentiation of floor plate cells by using the aforementioned (A) Neuro/B27, as compared to no addition of cAMP analogue and MEK inhibitor.

Experimental Example 2

Evaluation of Function of Dopaminergic Neuron Induced in Medium Added with dbcAMP and PD0325901

Floor plate cells were induced by a method similar to the methods described in Reference Examples 1 to 3, differentiation induction was performed by exchanging the medium with (A) Neuro/B27 added with 3 factors of ascorbic acid, dbcAMP and PD0325901, or (B) Neuro/B27 added with 2 factors of ascorbic acid and dbcAMP from day 13 of culture, and an ability to release dopamine by stimulation with high-KCl was evaluated on day 50 of culture.

Figure 7:
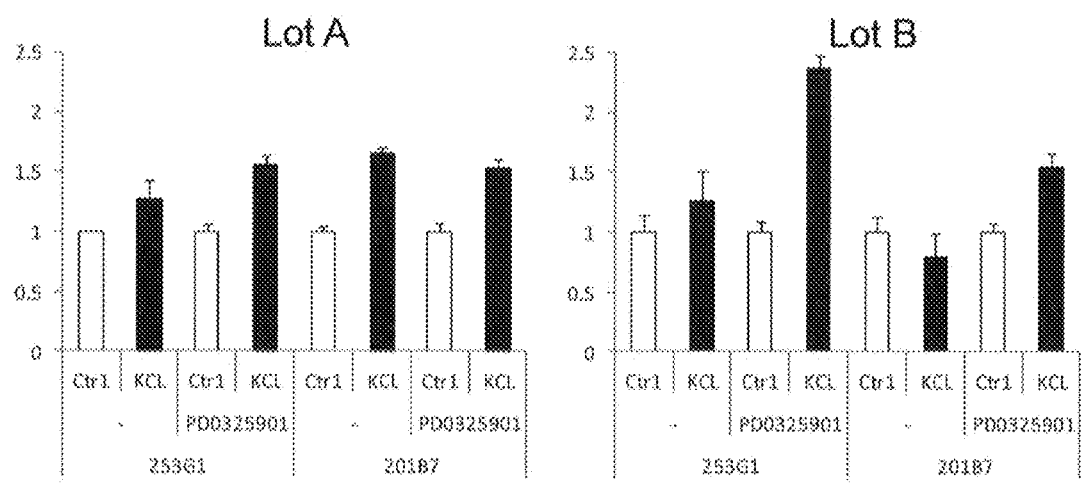
FIG. 7 shows the evaluation results of an ability to release dopamine by high-KCl stimulation on day 50 of culture, after differentiation induction in the same manner as in FIG. 5. As the cell lines, 253G1 strain and 201B7 strain were used, and the results of two independent experiments are shown. Ctrl shows stimulation condition with HBSS, and KCL shows stimulation condition with HBSS containing 55 mM KCl. The value of the Y axis shows the relative value when the amount of dopamine released in the control group is 1, and the error bar shows standard deviation.

The above-mentioned evaluation was performed as follows. The medium of the cells after differentiation induction was exchanged with Neuro/B27, and the cells were cultured overnight. The cells were incubated the next day in HBSS (Life Technologies, containing calcium and magnesium) at 37° C. under 5% $CO_2$ for 1 hr, the medium was exchanged with HBSS (control) or HBSS added with 55 mM KCl, and the cells were incubated at 37° C. under 5% $CO_2$ for 15-30 min. After incubation, the supernatant was recovered and passed through a filter (UFC30HVNB, Nihon Millipore K.K.). 0.01N HCl and 100 μM EDTA were added, and the obtained sample was preserved at −80° C. until analysis. For the analysis, a trace biological sample analysis system and HTEC500 (Eicom Corporation), electrochemical detector EPC-500 (Eicom Corporation) were used, and the amount of dopamine contained in the sample was measured according to the manual of Eicom Corporation (Eicom information No. 25). The results are shown in FIG. 7. By differentiation induction using the aforementioned (A) Neuro/B27, an increase in the amount of dopamine released by stimulation with high-KCl could be clearly detected. When differentiation was induced using the aforementioned (B) Neuro/B27, dopamine release was not observed depending on the lot. However, when differentiation was induced using the aforementioned (A) Neuro/B27, an increase in the amount of dopamine released by stimulation with high-KCl could be detected with good reproducibility even in a different lot. This suggests that PD0325901 stabilized the differentiation system. While the response was somewhat different between 253G1 and 201B7 strains, when PD0325901 was added, an increase in the amount of dopamine released by stimulation with high-KCl was stably detected, whereby an increase in the amount of dopamine released by high-KCl stimulation was confirmed between different cell lines.

Example 2

Study of Various MEK Inhibitors (Including FGFR Inhibitor)

Whether midbrain dopaminergic neuron can be induced in a medium containing any of PD184352 (Axon MedChem), SU5402 (FGF receptor (FGFR) inhibitor, Wako Pure Chemical Industries, Ltd.) and PD173074 (FGFR inhibitor, Axon MedChem) instead of PD0325901 in the aforementioned (A) Neuro/B27 was studied.

Floor plate cells were induced by a method similar to the methods described in Reference Examples 1 to 3, the medium was exchanged with Neuro/B27 added with (1) 3 factors of ascorbic acid, dbcAMP and PD0325901, (2) 2 factors of ascorbic acid and dbcAMP, (3) ascorbic acid, dbcAMP and 3 μM PD184352, (4) ascorbic acid, dbcAMP and 10 μM SU5402, or (5) ascorbic acid, dbcAMP and 0.1 μM PD173074 on day 13 of culture, and the cells were cultured at 37° C. under 5% $CO_2$ for not less than 30 days. The medium was exchanged every 3-4 days during the above-mentioned culture periods. On day 45 of culture, the cells were recovered, and expression variation of NURR1 was examined. The results are shown in FIG. 8. In 253G1 strain, the expression of NURR1 was elevated by the addition of PD0325901, PD184352 or SU5402 and, in 201B7 strain, the expression of NURR1 was elevated by the addition of all 4 kinds. On the other hand, PLX4032 known to activate the MEK pathway showed no effect.

From the above results, it was suggested that elevated expression of NURR1 is caused by a MEK (or FGFR in the upstream) inhibitory action.

Experimental Example 3

Figure 10:
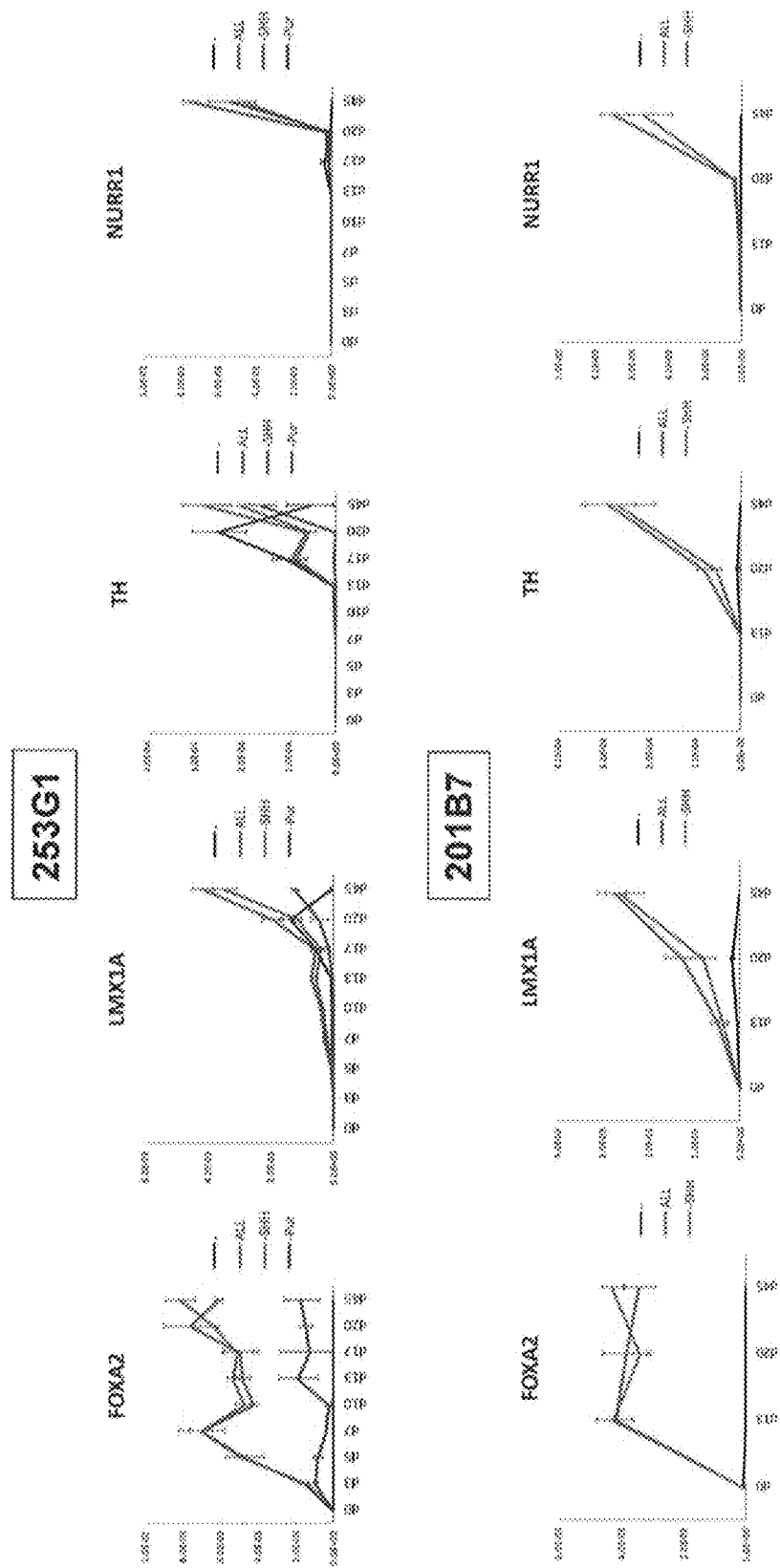
FIG. 10 shows the results of time-course expression variation of various differentiation markers as examined by quantitative RT-PCR, when differentiation induction was performed according to the method of FIG. 9. [All], [−], [−SHH], and [−Pur] show that the differentiation induction was performed according to FIG. 9, excluding CHIR99021, LDN193189, SB431542, SHH and purmorphamine, excluding SHH alone, and excluding purmorphamine alone, respectively. As the cell lines, 253G1 strain and 201B7 strain were used. The value of the Y axis shows the copy number of each gene normalized with the copy number of GAPDH, and the error bar shows standard deviation.

Expression Variation of Each Differentiation Marker in Differentiation Induction Process Based on the results of the above-mentioned Reference Examples, Examples and Experimental Examples, a dopaminergic neuron differentiation system consisting of the three steps shown in FIG. 9 was set, and expression of various differentiation markers in the differentiation induction process from undifferentiated iPS cell was examined In step 1, the cells were cultured in Neuro/B27 added with 0.5 μM LDN193189, 10 μM SB431542, 0.5 μM purmorphamine, 200 ng/ml SHH and 1 μM CHIR99021 for 5 days. In step 2, the cells were cultured in Neuro/B27 added with 0.5 μM LDN193189 and 1 μM CHIR99021 for 8 days (total 13 days). In step 3, the cells were cultured in Neuro/B27 added with 0.1 mM ascorbic acid, 0.5 mM dbcAMP and 3 μM PD0325901 for 32 days (total 45 days). After culture, time-course expression variation of various differentiation markers was measured by a method similar to Reference Example 3. The results of the expression analysis are shown in FIG. 10.

As a control, the cells were cultured under conditions without addition of a differentiation inducing factor (− in Figure), conditions excluding only SHH (−SHH in Figure) or conditions excluding only purmorphamine (−Pur in Figure). Also, the group subjected to differentiation induction under the conditions shown in FIG. 9 from step 2 onward was studied.

Under conditions added with all (All in Figure), the expression of floor plate cell marker FOXA2 was elevated up to day 7 of differentiation induction, and the expression level was maintained until completion of the differentiation induction. The expression of floor plate cell marker LMX1A for differentiation into the midbrain continued to elevate with time along with the differentiation induction. The expression of dopaminergic neuron markers TH and NURR1 drastically increased from day 20 of culture. On the other hand, an expression pattern similar to that under all added conditions (All in Figure) was also observed under conditions excluding only SHH (−SHH in Figure), which suggests that SHH is not essential. However, since expression of FOXA2 was low under conditions excluding only purmorphamine (−Pur in Figure), addition of purmorphamine is considered to be essential for the induction of floor plate cells.

Example 3

Efficiency of Differentiation Induction of Floor Plate Cells into Dopaminergic Neuron A factor that promotes differentiation into a dopaminergic neuron in step 3 in addition to PD0325901 was searched for. As a result, it was found that the efficiency of differentiation into a dopaminergic neuron is elevated when activin A is added in step 3.

Figure 11:
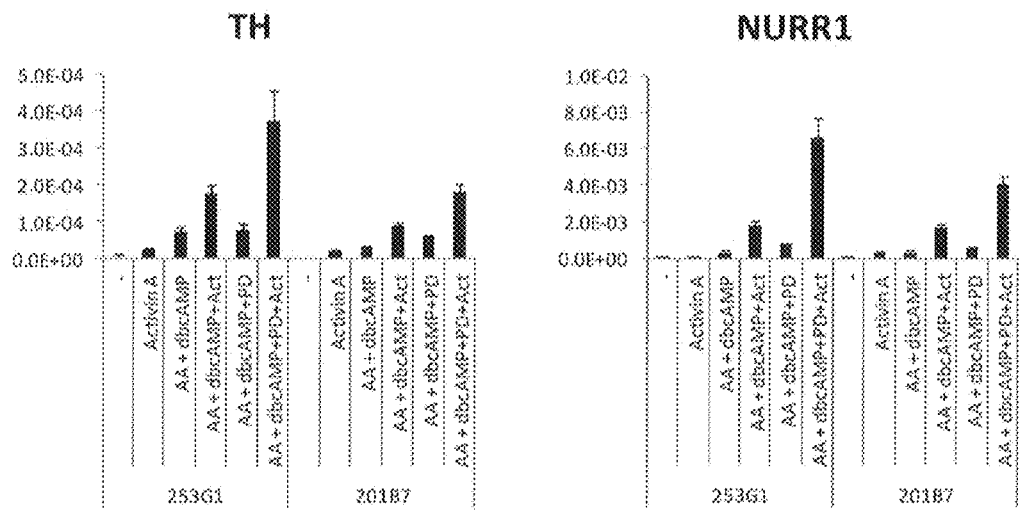
FIG. 11 shows the results of expression variation of dopaminergic neuron markers, which were obtained by inducing differentiation, in step 3 shown in FIG. 9, by adding various combinations of ascorbic acid (AA), dibutyryl-cAMP(dbcAMP), PD0325901(PD) and activin A(Act) and examining the expression variation of dopaminergic neuron markers by quantitative RT-PCR on day 26 of culture. [−] shows no addition of each differentiation inducing factor. As the cell lines, 253G1 strain and 201B7 strain were used. The value of the Y axis shows the copy number of each gene normalized with the copy number of GAPDH, and the error bar shows standard deviation.

Floor plate cells were induced by a method similar to the methods described in Reference Examples 1 to 3, the medium was exchanged with Neuro/B27 added with one or more kinds of 0.1 mM ascorbic acid, 0.5 mM dbcAMP, 3 μM PD0325901, and 20 ng/ml activin A (R&D), or Neuro/B27 without addition of ascorbic acid, dbcAMP, PD0325901, and activin A as a control on day 12 of culture, and the cells were cultured for 14 days more (total 26 days). The cells after culture were recovered, and the expression variation of TH and NURR1 was examined by a method similar to Reference Example 3. The results are shown in FIG. 11. When activin A alone was added, the expression of TH and NURR1 was scarcely elevated. However, when activin A was added together with ascorbic acid and dbcAMP, the expression of TH and NURR1 increased remarkably, and when PD0325901 was added together with ascorbic acid, dbcAMP and activin A, the expression was further elevated highly. On the other hand, when ascorbic acid, dbcAMP and PD0325901 were added, the expression level was lower at the time point of day 26 of culture than the addition of ascorbic acid, dbcAMP and activin A.

Figure 12:
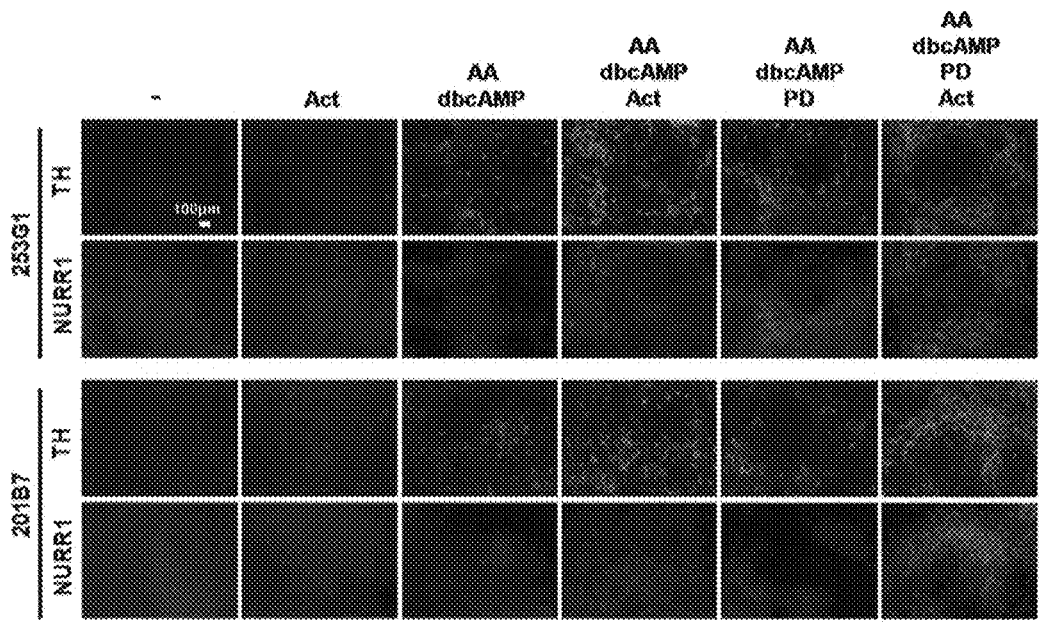
FIG. 12 shows the results of immunofluorescent staining using anti-TH antibody and anti-NURR1 antibody on day 26 of culture, after differentiation induction in the same manner as in FIG. 11. As the cell lines, 253G1 strain and 201B7 strain were used. Green shows the cell body of TH positive cells, and red shows the nucleus of NURR1 positive cells.

Next, the expression of dopaminergic neuron markers TH and NURR1 proteins was examined by immunofluorescent staining using anti-TH antibody and anti-NURR1 antibody. Floor plate cells were induced, the medium was exchanged with Neuro/B27 added with one or more kinds of 0.1 mM ascorbic acid, 0.5 mM dbcAMP, 3 μM PD0325901, and 20 ng/ml activin A, or Neuro/B27 without addition of a differentiation inducing factor as a control on day 12 of culture, and the cells were cultured for 14 days more (total 26 days). After culture, 4% PFA was added, and the cells were fixed at room temperature for 30 mM The cells were reacted with anti-TH antibody and anti-NURR1 antibody as the primary antibodies, and sequentially reacted with Alexa488-labeled secondary antibody and Alexa568-labeled secondary antibody, corresponding to the immunized animal of the primary antibody, as the secondary antibodies, and observed under a fluorescence microscope. The results are shown in FIG. 12. It was observed that simultaneous addition of ascorbic acid, dbcAMP, activin A and PD0325901 remarkably increased the cells expressing TH and NURR1 proteins. These results matched well with the results of expression variation of TH and NURR1 genes.

From the above results, it was clarified that midbrain dopaminergic neuron can be induced efficiently in a shorter differentiation induction period (total 26 days) than usual by the addition of ascorbic acid, dbcAMP, PD0325901 and activin A after induction of floor plate cells.

Experimental Example 4

Cryopreservation on Day 26 of Differentiation Induction

Midbrain floor plate cells were induced by a method similar to the methods described in Reference Examples 1 to 3, the medium was exchanged with Neuro/B27 added with 0.1 mM ascorbic acid, 0.5 mM dbcAMP, 3 μM PD0325901, and 20 ng/ml activin A (R&D) on day 12 of culture, and the cells were cultured for 14 days more (total 26 days). After culture, the cells were washed with PBS, and dispersed by treating with Accutase (Innovative Cell Technologies) at 37° C. for 20-30 min. After centrifugal washing, the cells were suspended in cell banker 2 (Juji Field Inc.) at a concentration of about $2 \times 10^6$ cells/ml/tube, and cryopreserved at −80° C.

The cryopreserved cells were thawed by immersion in a thermostatic tank at 37° C. and, after centrifugal washing, seeded in a 96 well plate at a density of $2 \times 10^4$ cells per well, and cultured at 37° C. under 5% $CO_2$ for 2 weeks. As the above-mentioned 96 well plate, one coated at 37° C. overnight with Matrigel 1/30-1/40 diluted with DMEM/F12 (Life Technologies Corporation) or Laminin (Trevigen Inc.) diluted with DMEM/F12 at a concentration of 10 μg/ml was used. As the culture medium, Neuro/B27 added with one or more kinds of 0.1 mM ascorbic acid, 0.5 mM dbcAMP, 3 μM PD0325901, and 20 ng/ml activin A, or Neuro/B27 without addition of ascorbic acid, dbcAMP, PD0325901, and activin A as a control was used.

Figure 13:
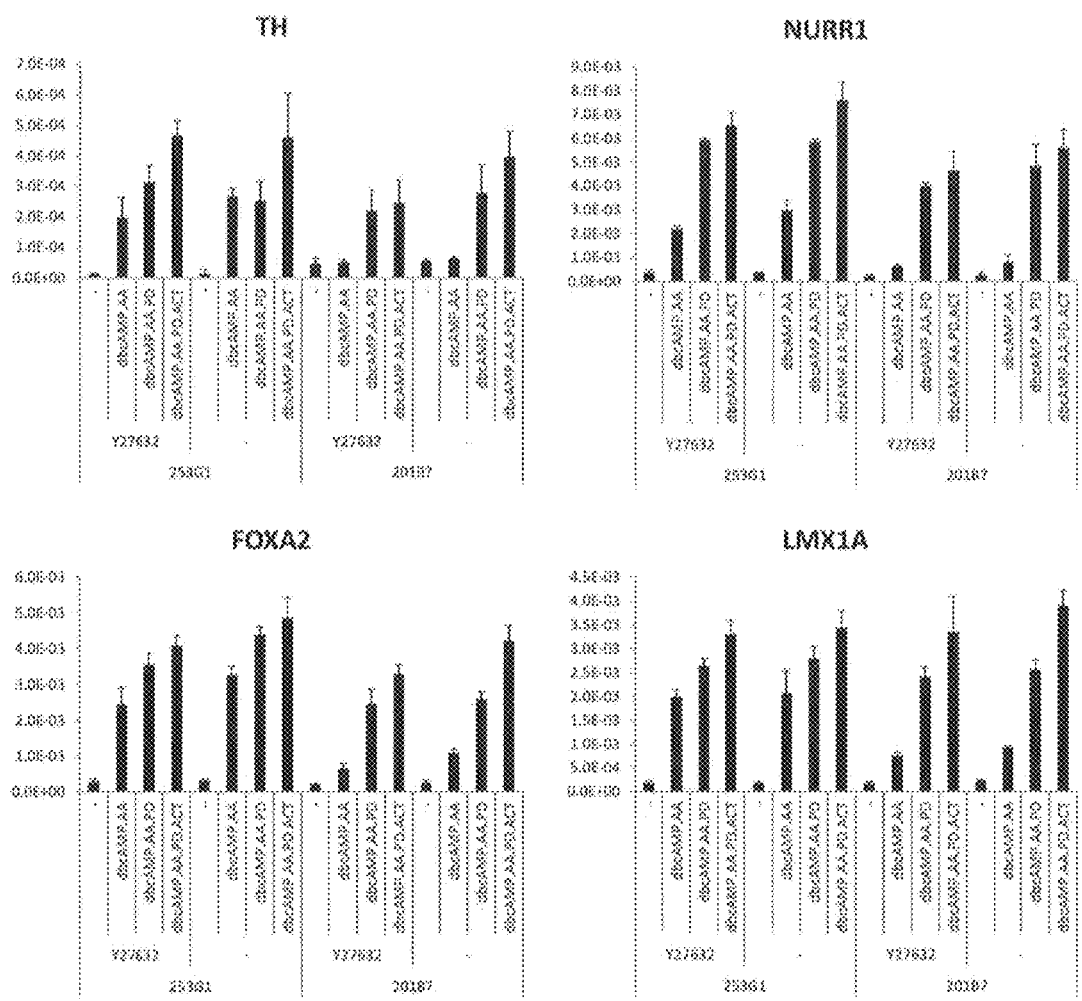
FIG. 13 shows the results of expression variation of dopaminergic neuron markers, which were obtained by inducing differentiation, in step 3 shown in FIG. 9, by adding various combinations of ascorbic acid (AA), dibutyryl-cAMP(dbcAMP), PD0325901(PD) and activin A(Act), cryopreserving the cells on day 26 of culture, thawing the cells, culturing the cells for 2 weeks by adding various combinations of AA, dbcAMP, PD and ACT, and examining the expression variation of dopaminergic neuron markers by quantitative RT-PCR on day 26 of culture. [−] shows no addition of each differentiation inducing factor. As the cell lines, 253G1 strain and 201B7 strain were used. The value of the Y axis shows the copy number of each gene normalized with the copy number of GAPDH, and the error bar shows standard deviation.

The cells cultured for 2 weeks after thawing were recovered, and the expression variation of dopaminergic neuron markers TH, NURR1, FOXA2 and LMX1A was examined by a method similar to Reference Example 3. The results are shown in FIG. 13. Each differentiation marker showed the highest expression when ascorbic acid, dbcAMP, activin A and PD0325901 were simultaneously added. When these factors were not added (− in Figure), the expression levels of the differentiation markers were low, which indicates that a differentiation factor is essential after thawing. The presence or absence of Y27632 (10 μM) in this case was also studied, and the expression levels of the markers were scarcely different.

Figure 14:
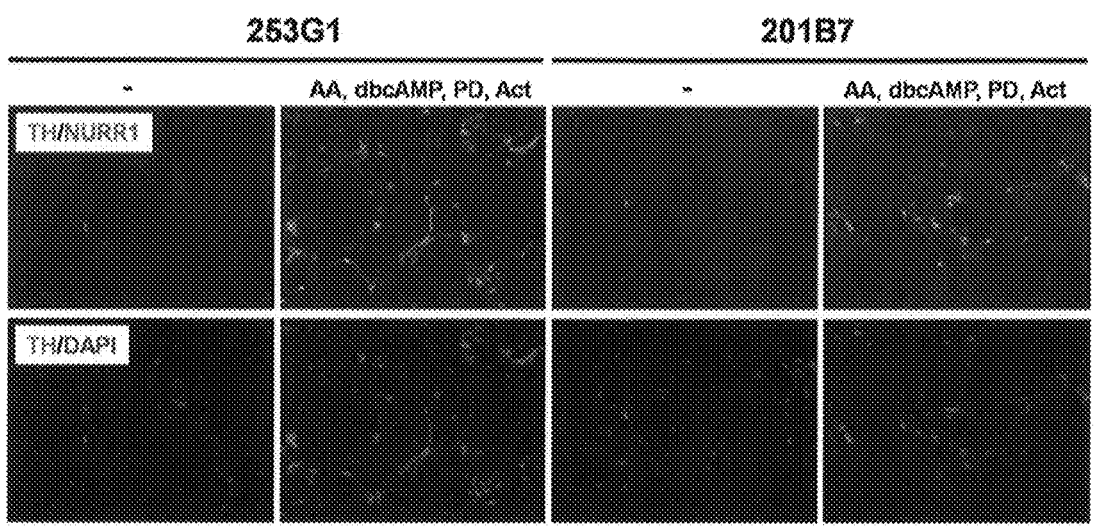
FIG. 14 shows the results of immunofluorescent staining, which were obtained by thawing the cryopreserved cells in the same manner as in FIG. 13, culturing the cells for 2 weeks by adding AA, dbcAMP, PD and ACT, and performing immunofluorescent staining using anti-TH antibody and anti-NURR1 antibody. Green shows the cell body of TH positive cells, red shows the nucleus of NURR1 positive cells, and blue (DAPI staining) shows the cell nucleus.

Next, the expression of TH and NURR1 proteins was examined by immunofluorescent staining using anti-TH antibody and anti-NURR1 antibody. 4% PFA was added to the cells cultured for two weeks after thawing, and the cells were fixed at room temperature for 30 min. The cells were reacted with anti-TH antibody and anti-NURR1 antibody as the primary antibodies, and sequentially reacted with Alexa488-labeled secondary antibody and Alexa568-labeled secondary antibody, corresponding to the immunized animal of the primary antibody, and observed under a fluorescence microscope. The results are shown in FIG. 14.

From the above results, it was clarified that the cells on day 26 of differentiation induction can be cryopreserved, and that a midbrain dopaminergic neuron that expresses TH and NURR1 proteins can be efficiently induced by culture with the addition of ascorbic acid, dbcAMP, activin A and PD0325901 after thawing.

Experimental Example 5

Transplantation Experiment

Midbrain floor plate cells were induced by a method similar to the methods described in Reference Examples 1 to 3, the medium was exchanged with Neuro/B27 added with 0.1 mM ascorbic acid, 0.5 mM dbcAMP, 3 µM PD0325901 or 0.1 mM ascorbic acid, 0.5 mM dbcAMP, 3 µM PD0325901, 20 ng/ml activin A on day 12 of culture, and the cells were cultured for 14 days more (total 26 days). After culture, the cells were washed with PBS, and dispersed by treating with TrypLE Express (Life Technologies) at 37° C. for 10 min. The cell concentration was adjusted to $1\times10^5$ cells/µl with Neuro/B27 medium, and the cells were maintained on ice until transplantation.

A transplantation experiment to mouse striatum was performed as follows. Twelve 8-week-old male NOD SCID mice (Charles River Laboratories Japan, Inc.) were divided into a control group and an activin A group (6 mice per each group). The cells cultured with the addition of ascorbic acid, dbcAMP, PD0325901 were used for transplantation to the control group, and the cells cultured with the addition of ascorbic acid, dbcAMP, PD0325901, activin A were used for transplantation to the activin A group. The hair of the head surgical field of the mice was shaved under pentobarbital (50 mg/kg, ip) anesthesia, and isodine was applied. Several minutes later, the skin was disinfected by wiping off isodine with Menban immersed in 0.1% Osvan aqueous solution, and the mice were fixed on a brain stereotaxis apparatus (David Kopf, David Kopf Instruments in USA). The scalp was incised from the midline, periosteum was detached, and Bregma and Lambda of the mice were exposed. "The mouse brain in stereotaxic coordinates" was referred to for the coordinate of the striatum (AP: +0.5 mm; ML: +1.8 mm), a hole was made in the cranial bone with an electric drill (φ0.5 mm), Hamilton syringe was inserted from the surface of the cranial bone to the depth DV: −3.5 mm, and the cells ($1\times10^5$ cells/µl, 2 µl) were transplanted over 10 min After transplantation, the incision on the head was sutured and the mice were allowed to recover. At 4 weeks, 8 weeks and 12 weeks after the transplantation, two mice from each group were sampled. Under isoflurane inhalation anesthesia, the mice were exsanguinated by decapitation, and the head was fixed with 4% para-formaldehyde for 24 hr. After the cranial bone was removed, the brain was dehydrated with 30% saccharose solution for 24 hr. Thereafter, the brain was freeze-embedded, and frozen section (40 µm) was prepared using a cryostat (Leica CM3050S). The tissue staining of the dopaminergic neuron was performed using anti-TH antibody and anti-human specific Nuclei antibody (MAB1281, Nihon Millipore K.K.) (hNuc).

Figure 15:
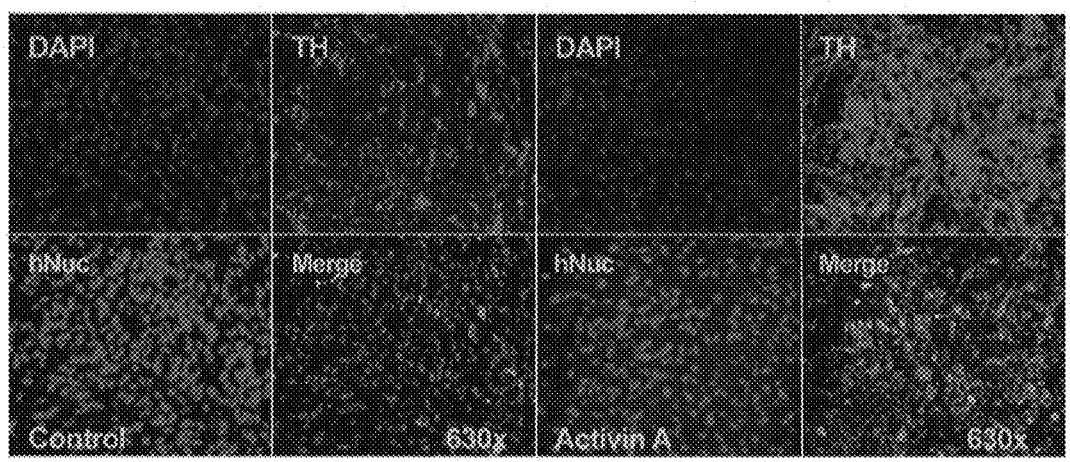
FIG. 15 shows the results of tissue staining, which were obtained by inducing differentiation, in step 3 shown in FIG. 9, by adding ascorbic acid, dbcAMP, PD0325901 (control group; four pieces of panels on the left side) or ascorbic acid, dbcAMP, PD0325901 and activin A (Activin A group; four pieces of panels on the right side), recovering the cells on day 26 of culture, transplanting the cells to the mouse striatum, and performing tissue staining 4 weeks after the transplantation. Green shows the cell body of TH positive cells, red shows the nucleus of hNuc positive cells, and blue (DAPI staining) shows the cell nucleus.
Figure 16:
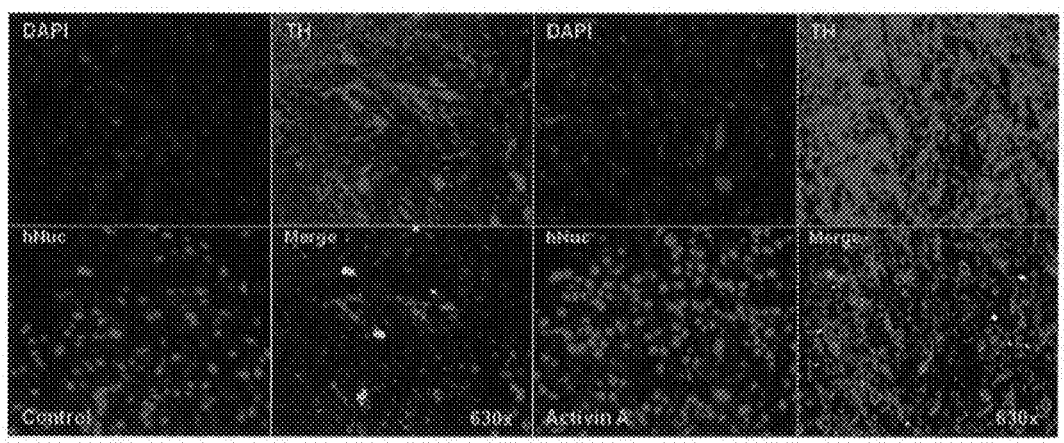
FIG. 16 shows the results of tissue staining after transplantation in the same manner as in FIG. 15 and at 8 weeks after the transplantation. Green shows the cell body of TH positive cells, red shows the nucleus of hNuc positive cells, and blue (DAPI staining) shows the cell nucleus.
Figure 17:
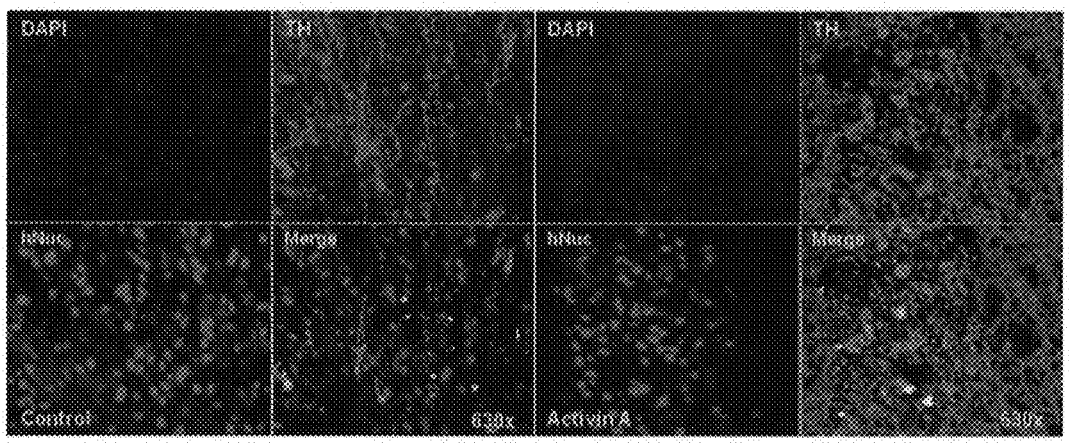
FIG. 17 shows the results of tissue staining after transplantation in the same manner as in FIG. 15 and at 12 weeks after the transplantation. Green shows the cell body of TH positive cells, red shows the nucleus of hNuc positive cells, and blue (DAPI staining) shows the cell nucleus.

After 4 weeks from the transplantation, TH/hNuc double positive cells were slightly (not more than 5%) observed in the mouse striatum of the control group (FIG. 15, left), whereas many TH/hNuc double positive cells (not less than 40%, FIG. 15, right) were observed in the activin A group. After 8 weeks from the transplantation, TH/hNuc double positive cells increased in the brain section of the control group as compared to that of 4 weeks, and TH/hNuc double positive cells further increased to not less than 50% in the activin A group as compared to that of 4 weeks (FIG. 16). After 12 weeks from the transplantation, TH/hNuc double positive cells further increased to less than 10% in the brain section of the control group as compared to that of 8 weeks. In the activin A group, TH/hNuc double positive cells did not show a remarkable increase as compared to 8 weeks (FIG. 17).

From the above results, it was clarified that midbrain floor plate cells cultured, after induction, in a medium added with ascorbic acid, dbcAMP, PD0325901 and activin A are efficiently differentiated into a dopaminergic neuron in the mouse striatum and continue to be colonized for not less than 3 months.

This application is based on patent application No. 2013-163062 filed in Japan (filing date: Aug. 6, 2013), the contents of which are encompassed in full herein.

INDUSTRIAL APPLICABILITY

According to the present invention, a high-quality dopaminergic neuron can be produced more efficiently from neural progenitor cells. The dopaminergic neuron produced by the present invention has phenotypic characteristics and functions similar to those of dopaminergic neurons in vivo, since it shows responsiveness to oxidative stress and drug stimulation that has not been observed in dopaminergic neurons produced by conventional methods, and the like. Therefore, the dopaminergic neuron produced by the present invention can achieve a high engrafted rate and is extremely useful for a cell transplantation therapy for treating a disease caused by decreased production (release) of dopamine, for example, neurodegenerative diseases such as Parkinson's disease and the like, as well as can be used for various applications such as screening for a compound useful for the prophylaxis and/or treatment of said diseases, toxicity evaluation of compounds, verification of drug discovery targets, analysis of disease mechanism and the like.

The invention claimed is:

1. A production method of a dopaminergic neuron, comprising subjecting floor plate cells to the following step (1):
   (1) a step of culturing in a medium containing (i) a cAMP analogue and (ii) a MEK inhibitor, wherein the MEK inhibitor is
   (i) PD0325901: N-[(2R)-2,3-dihydroxypropoxy]-3,4-difluoro-2-[(2-fluoro-4-iodo-phenyl) amino] benzamide,
   (ii) PD184352: 2-(2-chloro-4-iodophenylamino)-N-cyclopropylmethoxy-3,4-difluorobenzamide, or
   (iii) SU5402: 2-[(1,2-dihydro-2-oxo-3H-indol-3-ylidene) methyl]-4-methyl-1H-pyrrole-3-propanoic acid.

2. The production method according to claim 1, wherein the medium is a medium further containing ascorbic acid or a salt thereof.

3. The production method according to claim 2, wherein the medium is a medium further containing an activator of activin receptor-like kinase-4,7.

4. The production method according to claim 1, wherein the cAMP analogue is dibutyryl-cAMP.

5. The production method according to claim 3, wherein the activator of activin receptor-like kinase-4,7 is activin.

6. The production method according to claim 3, wherein the cAMP analogue is dibutyryl-cAMP,
and
the activator of activin receptor-like kinase-4,7 is activin.

7. The production method according to claim 1, wherein the medium comprises Base Medium, and Medium Supplement A.

8. The production method according to claim 7, wherein a concentration of Medium Supplement A in the medium is 0.1-10 wt %.

9. The production method according to claim 8, wherein the concentration of Medium Supplement A in the medium is 2 wt %.

10. The production method according to claim 7, wherein the medium further comprises Medium Supplement B.

* * * * *